US006511962B1

(12) United States Patent
Borders et al.

(10) Patent No.: US 6,511,962 B1
(45) Date of Patent: Jan. 28, 2003

(54) DERIVATIVES OF LASPARTOMYCIN AND PREPARATION AND USE THEREOF

(75) Inventors: Donald B Borders, Suffern, NY (US); William V Curran, Pearl River, NY (US); Amedeo A Fantini, New City, NY (US); Noreen D Francis, Harriman, NY (US); Howard Jarolmen, Upper Saddle River, NJ (US); Richard A Leese, Suffern, NY (US)

(73) Assignee: Micrologix Biotech Inc., Vancouver (CA)

( * ) Notice: Subject to any disclaimer, the term of this patent is extended or adjusted under 35 U.S.C. 154(b) by 0 days.

(21) Appl. No.: 09/760,328

(22) Filed: Jan. 12, 2001

Related U.S. Application Data

(60) Provisional application No. 60/219,059, filed on Jul. 17, 2000, and provisional application No. 60/220,950, filed on Jul. 26, 2000.

(51) Int. Cl.$^7$ .......................... A61K 38/12; C07K 7/56; C12P 21/04

(52) U.S. Cl. ....................... 514/11; 435/68.1; 435/71.3; 530/317

(58) Field of Search ......................... 514/9.11; 530/317, 530/321; 435/68.1, 71.3

(56) References Cited

U.S. PATENT DOCUMENTS

| | | | | |
|---|---|---|---|---|
| 3,639,582 A | * | 2/1972 | Umezawa et al. | 424/118 |
| 3,817,973 A | | 6/1974 | Bouchaudon et al. | 530/319 |
| 4,331,594 A | | 5/1982 | Hamill et al. | 260/112.5 R |
| 4,495,348 A | | 1/1985 | Kunishima et al. | 544/21 |
| 4,524,135 A | | 6/1985 | Abbott et al. | 435/69 |
| 4,800,157 A | | 1/1989 | Eaton et al. | 435/71 |
| 4,977,083 A | | 12/1990 | Boeck | 435/71.3 |
| 4,994,270 A | | 2/1991 | Boeck et al. | 514/9 |
| 5,028,590 A | | 7/1991 | Fukuda et al. | 514/11 |
| 5,039,789 A | | 8/1991 | Fukuda et al. | 530/317 |
| 5,629,288 A | * | 5/1997 | Lattrell et al. | 514/9 |
| 5,912,226 A | | 6/1999 | Baker et al. | 514/9 |
| 6,146,872 A | | 11/2000 | Ueda et al. | 435/231 |
| 6,194,383 B1 | | 2/2001 | Hammann et al. | 514/11 |

FOREIGN PATENT DOCUMENTS

| | | | |
|---|---|---|---|
| WO | WO98/00173 | A2 | 1/1998 |
| WO | WO99/21869 | A1 | 5/1999 |

OTHER PUBLICATIONS

Naganawa et al. A Novel Fatty Acid From Laspartomycin. The journal of Antibiotics, vol. 23, No. 8, pp. 423–424, Aug. 1970.*

BodansZky et al., "Structure of the Peptide Antibiotic Amphomycin", Journal of the Amer. Chem. Soc., 95:7, Apr. 4, 1973, pp. 2352–2357.

Debono et al., "Enzymatic and Chemical Modifications of Lipopeptide Antibiotic A21978C: The Synthesis and Evaluation of Daptomycin (LY146032)", The Journal of Antibiotics, vol. XLI, No. 8, Aug. 1988, pp. 1093–1105.

Shay et al., "Aspartocin. I. Production, Isolation, and Characteristics", Antibiotics Annual 1959–1960, pp. 194–198.

Naganawa et al., "Laspartomycin, A New Anti–Staphylococcal Peptide", The Journal of Antibiotics, vol. 21:1, Jan. 1968, pp. 55–62.

Martin et al., "Isolation and Identification of D–α–Pipecolic Acid, α[L],β–Methylaspartic Acid and α,β–Diaminubutyric Acid from the Polypeptide Antibiotic Aspartocin", Communications to the Editor, Apr. 20, 1960, pp. 2079.

* cited by examiner

*Primary Examiner*—Jeffrey E. Russel
(74) *Attorney, Agent, or Firm*—Seed Intellectual Property Law Group PLLC

(57) ABSTRACT

The present invention provides a laspartomycin core peptide, a laspartomycin core peptide derivative, a antimicrobial laspartomycin derivative, a method for making laspartomycin core peptides, methods for making laspartomycin core peptide derivatives, methods for making antimicrobial laspartomycin derivatives, pharmaceutical compositions of antimicrobial laspartomycin derivatives, methods of inhibiting microbial growth and methods for treating and/or preventing microbial infections in a subject.

80 Claims, No Drawings

DERIVATIVES OF LASPARTOMYCIN AND PREPARATION AND USE THEREOF

This application claims the benefit under 35 U.S.C. §119(e) of U.S. Provisional Application No. 60/219,059, filed Jul. 17, 2000 and U.S. Provisional Application No. 60/220,950, filed Jul. 26, 2000, which are incorporated herein by reference in their entirety.

1. FIELD OF THE INVENTION

The present invention relates generally to antibiotics and antimicrobial derivatives. More particularly, the present invention relates to intermediates useful for synthesizing laspartomycin derivatives as well as the laspartomycin derivatives.

2. BACKGROUND OF THE INVENTION

Laspartomycin (Umezawa et al., U.S. Pat. No. 3,639,582; Naganawa et al., 1968, *J. Antibiot.*, 21, 55; Naganawa et al., 1970, *J. Antibiot.*, 23, 423 which are herein incorporated by reference) is closely related to antibiotics such as zaomycin (Kuroya, 1960, *Antibiotics Ann.*, 194; Kuroya, JP 8150), crystalomycin (Gauze et al., 1957, *Antibiotiki*, 2, 9), aspartocin (Shay et al., 1960, *Antibiotics Annual*, 194; Hausman et al., 1964, *Antimicrob. Ag. Chemother.*, 352; Hausman et al., 1969, *J. Antibiot.*, 22, 207; Martin et al., 1960, *J. Am. Chem. Soc.*, 2079), amphomycin (Bodanszky et. al., 1973, *J. Am. Chem. Soc.*, 95, 2352), glumamycin (Fujino et al., 1965, *Bull. Chem. Soc. Jap.*, 38, 515), daptomycin (Debono et. al., 1988, *J. Antibiotics*, 41, 1093), Antibiotic A-1437 (Hammann et. al., EP 0 629 636 B1; Lattrell et al., U.S. Pat. No. 5,629,288), Antibiotic A54145 (Fukada et al., U.S. Pat. No. 5,039,789; Boeck et al., 1990, *J. Antibiotics*, 43, 587), and tsushimycin (Shoji et. al., 1968, *J. Antibiot.*, 21, 439). The above compounds are lipopeptide antibiotics which typically inhibit gram positive bacteria. Generally, lipopeptide antibiotics consist of either a cyclic core peptide or a cyclic core depsipeptide acylated with a lipophilic fragment such as an unsaturated fatty acid.

Laspartomycin, produced by fermenting the microorganism *Streptomyces viridochromogenes* var. *komabensis*, was first isolated while screening for compounds active against resistant staphylococci (Naganawa et al., 1968, *J. Antibiot.*, 21, 55; Umezawa et al., U.S. Pat. No. 3,639,582). Laspartomycin was characterized by conventional methods and was shown to be active against a variety of gram positive bacteria, including staphylococci and some fungi (id.). Elemental analysis and amino acid analysis provided a molecular weight of about 1827 for the lipopeptide antibiotic, while amino acid analysis indicated the presence of the amino acids threonine and diaminobutryic acid in the peptide portion of laspartomycin (id.).

In other studies, the major lipophilic fragment of laspartomycin was shown to be trans-2-isopentadecanoic acid 2, illustrated below (Naganawa et al., 1970, *J. Antibiot.* 23, 423). In contrast, the lipophilic portions of antibiotics such as aspartocin (Hausmann et al., 1963, *Antimicr. Agents & Chemoth.*, 352, 1962), glumamycin (Inoue, 1962, *Bull. Chem. Soc. Jap.*, 35, 1255), tsushimycin (Shoji et al., 1968, *J. Antibiot.*, 21, 439) and amphomycin (Shoji et al., 1969, *J. Antibiot.*, 22, 473) are all derived from cis β-γ unsaturated carboxylic acids.

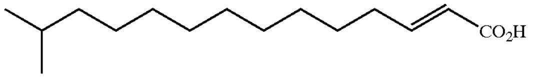

The results described in the instant Application indicate that the amino acid analysis and the molecular weight disclosed in the art are incorrect (Umezawa et al., U.S. Pat. No. 3,639,582; Naganawa et al., 1968, *J. Antibiot.*, 21, 55). In particular current studies disclosed in this Application show that the peptide core of laspartomycin contains novel amino acids not found in other known lipopeptide antibacterial antibiotics. For example, laspartomycin is the only member of the antibacterial lipopeptide family that contains diaminopropionic acid in the peptide core. Amphomycin, aspartocin, zaomycin, tsushimycin, and antibiotic A-1437 contain, instead, 2,3-diaminobutyric acid in the peptide portion of the molecule (Kuroya, 1960, *Antibiotics Ann.*, 194; Gauze et al.,1957, *Antibiotiki*, 2, 9; Shay et al., 1960, *Antibiotics Annual*, 194–198; Hausman et al., 1964, *Antimicrob. Ag. Chemother.*, 352; Hausman et al., 1969, *J. Antibiot.*, 22, 207; Martin et al., 1960, *J. Am. Chem. Soc.*, 2079; Bodanszky et. al., 1973, *J. Am. Chem. Soc.*, 95, 2352; Fujino et al., 1965, *Bull. Chem. Soc. Jap.*, 38, 515; Hammann et. al., EP 0 629 636 B1; Lattrell et al., U.S. Pat. No. 5,629,288; Shoji et al., 1968, *J. Antibiot.*, 21, 439). Additionally, laspartomycin contains allothreonine, which is not found in the other known lipopeptides. Further laspartomycin is the smallest of the known lipopeptides with a molecular weight of about 1247 for the cyclic core peptide acylated with compound 2.

Despite the efficacy of laspartomycin against gram positive bacteria, the medicinal chemistry of this lipopeptide antibacterial antibiotic has remained largely unexplored. However, given the recent dramatic rise of antibiotic-resistant pathogens and infectious diseases, caused in part, by frequent over use of antibiotics, the need for new antimicrobial agents is urgent (Cohen et al., 1992, *Science*, 257, 1050–1055). Specifically, methicillin resistant bacteria are a particular problem since they are also resistant to a wide variety of antibiotics other than methicillin (Yoshida et al., U.S. Pat. No. 5,171,836). Gram positive bacteria, such as Staphylococci, which cause persistent infections, are especially dangerous when methicillin resistant. Even more alarmingly, strains of *Enterococcus faecium* that are resistant to vancomycin have been recently observed (Moellering, 1990, *Clin. Microbiol. Rev.*, 3, 46). Strains resistant to vancomycin pose a serious health threat to society since vancomycin is the antibiotic of last resort for several harmful pathogens. Thus, there is a general need for antibiotic agents and a specific need for antibiotic agents that are active against microbes resistant to methicillin or vancomycin.

3. SUMMARY OF THE INVENTION

The present invention addresses this and other needs in the art by providing antimicrobial laspartomycin derivatives, pharmaceutical compositions of antimicrobial laspartomycin derivatives, methods for making antimicrobial laspartomycin derivatives, methods for inhibiting microbial growth and methods for treating or preventing microbial infections in a subject. The present invention also provides a laspartomycin core peptide, methods for making the laspartomycin core peptide and a laspartomycin core peptide derivative and methods for making the laspartomycin core peptide derivative all of which are all useful in synthesizing antimicrobial laspartomycin derivatives.

In one aspect, the present invention provides a laspartomycin core peptide derivative that may be used as a key intermediate in the synthesis of antimicrobial laspartomycin derivatives. An essential part of the laspartomycin core peptide derivative is a core cyclic peptide attached to a nitrogen atom which may be part of a variety of functional groups such as, for example, a carbamate, amide or sulfonamide.

In one embodiment, the laspartomycin core peptide derivative includes a linker which is typically attached to the nitrogen of the core cyclic peptide. The linker may be derived from compounds such as amino acids, polyamides, polyamines, polyethers, polysulfonamides or other linkers known to those of skill in the art. The linker typically includes a linking group which may be any chemical functionality that can participate in covalent bond formation. The linking group provides a site for further modification of the laspartomycin core peptide derivative. For example, the linking group may be modified with a lipophilic moiety to provide a laspartomycin derivative of the invention.

Thus, in one illustrative embodiment, the present invention provides a laspartomycin core peptide derivative according to structural formula (I):

$$Y^1—L—X^1—N(R^1)—R \qquad (I)$$

or a salt or hydrate thereof, wherein either:

(i) $Y^1$—L—$X^1$ taken together is hydrogen; or (ii) $Y^1$ is a linking group;

L is a linker;

$X^1$ is selected from the group consisting of —CO—, —$SO_2$—, —CS—, —PO—, —OPO—, —OC(O)—, —NHCO— and —$NR^1$CO—;

N is nitrogen;

$R^1$ is selected from the group consisting of hydrogen, ($C_1$–$C_{10}$) alkyl optionally substituted with one or more of the same or different $R^2$ groups, ($C_1$–$C_{10}$) heteroalkyl optionally substituted with one or more of the same or different $R^2$ groups, ($C_5$–$C_{10}$) aryl optionally substituted with one or more of the same or different $R^2$ groups, ($C_5$–$C_{15}$) arylaryl optionally substituted with one or more of the same or different $R^2$ groups, ($C_5$–$C_{15}$) biaryl optionally substituted with one or more of the same or different $R^2$ groups, five to ten membered heteroaryl optionally substituted with one or more of the same or different $R^2$ groups, ($C_6$–$C_{16}$) arylalkyl optionally substituted with one or more of the same or different $R^2$ groups and six to sixteen membered heteroarylalkyl optionally substituted with one or more of the same or different $R^2$ groups;

each $R^2$ is independently selected from the group consisting of —$OR^3$, —$SR^3$, —$NR^3R^3$, —CN, —$NO_2$, —$N_3$, —C(O)$OR^3$, —C(O)$NR^3R^3$, —C(S)$NR^3R^3$, —C($NR^3$)$NR^3R^3$, —CHO, —$R^3$CO, —$SO_2R^3$, —$SOR^3$, —PO($OR^3$)$_2$, —PO($OR^3$), —$CO_2$H, —$SO_3$H, —$PO_3$H, halogen and trihalomethyl;

each $R^3$ is independently selected from the group consisting of hydrogen, ($C_1$–$C_6$) alkyl, ($C_5$–$C_{10}$) aryl, 5–10 membered heteroaryl, ($C_6$–$C_{16}$) arylalkyl and six to sixteen membered heteroarylalkyl; and R is the core cyclic peptide of laspartomycin.

In another aspect, the present invention provides antimicrobial laspartomycin derivatives. The antimicrobial laspartomycin derivatives are generally laspartomycin core peptide derivatives of the invention that have been further modified with a lipophilic moiety. The lipophilic moiety will usually be attached to a linking group covalently bonded to the nitrogen atom of the core peptide derivative.

Thus, in another illustrative embodiment, the present invention provides an antimicrobial laspartomycin derivative according to structural formula (II):

$$Y^2—(X^2—X^3)—(L)—(X^1)—N(R^1)—R \qquad (II)$$

or a pharmaceutically acceptable salt or hydrate thereof, wherein:

$Y^2$ is a lipophilic group;

$X^1$ is selected from the group consisting of —CO—, —$SO_2$—, —CS—, —PO—, —OPO—, —OC(O)—, —NHCO— and —$NR^1$CO—;

$X^2$ is a linked group;

$X^3$ is a linked group; and

N, L, $R^1$ and R are as previously defined for Formula (I).

In a third aspect, the present invention provides a method for making a laspartomycin core peptide that includes culturing the microorganism *Streptomyces viridochromogenes*, ssp. *komabensis* (ATCC 29814) in a culture medium to provide laspartomycin. Isolation of laspartomycin followed by cleavage of a lipophilic fragment provides the laspartomycin core peptide.

In a fourth aspect, the present invention provides methods for synthesizing a laspartomycin core peptide derivative. A linking moiety may be covalently attached to a laspartomycin core peptide to provide a laspartomycin core peptide derivative.

In a fifth aspect, the present invention provides approaches for synthesizing antimicrobial laspartomycin derivatives. In a first method, a linking moiety may be covalently attached to a laspartomycin core peptide to yield a laspartomycin core peptide derivative. Then, a lipophilic group may be covalently attached to the laspartomycin core peptide derivative to provide an antimicrobial laspartomycin derivative. In a second method, a linking moiety may be covalently attached to a lipophilic group to yield a linker-lipophilic group. Then the linker-lipophilic group may be covalently attached to the laspartomycin core peptide to provide an antimicrobial laspartomycin derivative.

In a sixth aspect, the present invention provides pharmaceutical compositions comprising the antimicrobial laspartomycin derivatives of the invention. The pharmaceutical compositions generally comprise one or more antimicrobial laspartomycin derivatives of the invention, and/or pharmaceutically acceptable salts thereof and a pharmaceutically acceptable carrier, excipient or diluent. The choice of carrier, excipient or diluent will depend upon, among other factors, the desired mode of administration.

In a seventh aspect, the present invention provides methods of inhibiting the growth of microbes such as gram positive bacteria, particularly, methicillin resistant *Staphylococcus aureus* and vancomycin resistant enterococci. The method generally involves contacting a microbe with one or more antimicrobial laspartomycin derivatives of the invention (or a pharmaceutically-acceptable salt thereof) in an amount effective to inhibit the growth of the microbe. The method may be practical to achieve a bacteriostatic effect, where the growth of the microbe is inhibited, or to achieve a bactericidal effect, where the microbe is killed.

In a final aspect, the present invention provides methods for treating and/or preventing microbial infections in a subject such as human, plant or animal. The methods generally involve administering to a subject one or more of the antimicrobial laspartomycin derivatives or pharmaceutical compositions of the invention in an amount effective to treat or prevent a microbial infection in the human, animal or plant. The antimicrobial laspartomycin derivatives or pharmaceutical compositions may be administered systemically or applied topically, depending on the nature of the microbial infection.

4. DETAILED DESCRIPTION OF THE INVENTION

4.1 Definitions

As used herein, the following terms are intended to have the following meanings.

"Laspartomycin:" refers to a mixture of at least three different compounds produced by culturing the microorganism *Streptomyces viridochromogenes*, ssp. *komabensis* (ATCC 29814) in a culture medium. It should be understood that the structure of the lipophilic side chain is different in the three compounds.

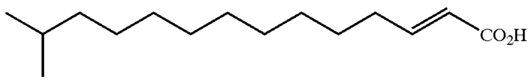

The major component of laspartomycin (typically around 80% under the fermentation and processing conditions used in this Application) is acylated with the C-15 α-β unsaturated carboxylic acid 2 shown above to provide C-15 laspartomycin 4 shown below.

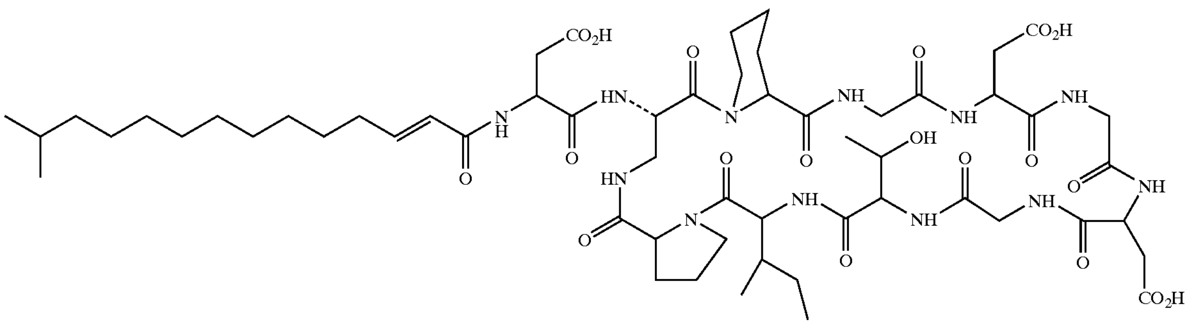

The two minor components are the C-14 and C-16 analogues of the C-15 α-β unsaturated carboxylic acid 2 shown above. The formulation of the culture medium and the ratio of the medium constituents has a direct effect on the ratio of the components of laspartomycin. Thus, no particular component composition is intended by the use of the term "laspartomycin."

"Lipophilic fragment:" refers to any lipophilic moiety attached to the laspartomycin core peptide that is produced by culturing the microorganism *Streptomyces viridochromogenes*, ssp. *komabensis* (ATCC 29814) in a culture medium. Thus, lipophilic fragments include but are not limited to, the C-14, C-15 and C-16 acyl analogues of the C-14, C-15 and C-16 α-β unsaturated carboxylic acids described above.

"Core cyclic peptide:" refers to the cyclic peptide portion of laspartomycin R shown below:

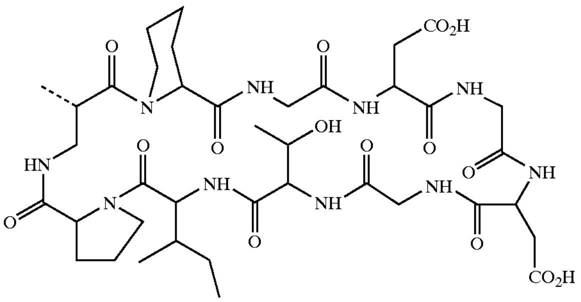

The dashed line indicates the carbon atom which is bonded to nitrogen in Formulas (I), (II) and (III).

"Laspartomycin core peptide:" refers to the peptide portion of laspartomycin after cleavage of at least the lipophilic fragment. The laspartomycin core peptide may be represented by Formula (III) shown below:

$R^xNHR$ (III)

where $R^x$ is either H or $NH_2CH(CH_2CO_2H)CO$— and R is the core cyclic peptide of laspartomycin as defined above.

"Alkyl" refers to a saturated or unsaturated, branched, straight-chain or cyclic monovalent hydrocarbon group derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. The expression "lower alkyl" refers to alkyl groups comprising from 1 to 8 carbon atoms.

"Alkanyl" refers to a saturated branched, straight-chain or cyclic alkyl group. Typical alkanyl groups include, but are not limited to, methanyl; ethanyl; propanyls such as propan-1-yl, propan-2-yl (isopropyl), cyclopropan-1-yl, etc.; butyanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" refers to an unsaturated branched, straight-chain or cyclic alkyl group having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" refers to an unsaturated branched, straight-chain or cyclic alkyl group having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is ($C_5$–$C_{14}$) aryl, with ($C_5$–$C_{10}$) being even more preferred. Particularly preferred aryls are cyclopentadienyl, phenyl and naphthyl.

"Arylaryl:" refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. Where the number of carbon atoms in an arylaryl group are specified, the numbers refer to the carbon atoms comprising each parent aromatic ring. For example, ($C_5$–$C_{14}$) arylaryl is an arylaryl group in which each aromatic ring comprises from 5 to 14 carbons, e.g., biphenyl, triphenyl, binaphthyl, phenylnaphthyl, etc. Preferably, each parent aromatic ring system of an arylaryl group is independently a ($C_5$–$C_{14}$) aromatic, more preferably a ($C_5$–$C_{10}$) aromatic. Also preferred are arylaryl groups in which all of the parent aromatic ring systems are identical, e.g., biphenyl, triphenyl, binaphthyl, trinaphthyl, etc.

"Biaryl:" refers to an arylaryl group having two identical parent aromatic systems joined directly together by a single bond. Typical biaryl groups include, but are not limited to, biphenyl, binaphthyl, bianthracyl, and the like. Preferably, the aromatic ring systems are ($C_5$–$C_{14}$) aromatic rings, more preferably ($C_5$–$C_{10}$) aromatic rings. A particularly preferred biaryl group is biphenyl.

"Arylalkyl" refers to an acyclic alkyl group in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In preferred embodiments, the arylalkyl group is ($C_6$–$C_{20}$) arylalkyl, e.g., the alkanyl, alkenyl or alkynyl moiety of the arylalkyl group is ($C_1$–$C_6$) and the aryl moiety is ($C_5$–$C_{14}$). In particularly preferred embodiments the arylalkyl group is ($C_6$–$C_{13}$), e.g., the alkanyl, alkenyl or alkynyl moiety of the arylalkyl group is ($C_1$–$C_3$) and the aryl moiety is ($C_5$–$C_{10}$).

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuiran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5–14 membered heteroaryl, with 5–10 membered heteroaryl being particularly preferred. The most preferred heteroaryl groups are those derived from thiophene, pyrrole, benzothiophene, benzofuran, indole, pyridine, quinoline, imidazole, oxazole and pyrazine.

"Heteroarylalkyl" refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylakenyl and/or heterorylalkynyl is used. In preferred embodiments, the heteroarylalkyl group is a 6–20 membered heteroarylalkyl, e.g., the alkanyl, alkenyl or alkynyl moiety of the heteroarylalkyl is 1–6 membered and the heteroaryl moiety is a 5–14-membered heteroaryl. In particularly preferred embodiments, the heteroarylalkyl is a 6–13 membered heteroarylalkyl, e.g., the alkanyl, alkenyl or alkynyl moiety is 1–3 membered and the heteroaryl moiety is a 5–10 membered heteroaryl.

"Substituted:" refers to a group in which one or more hydrogen atoms are each independently replaced with the same or different substituent(s). Typical substituents include, but are not limited to, —X, —$R^6$, —$O^-$, =O, —OR, —$SR^6$, —$S^-$, =S, —$NR^6R^6$, =$NR^6$, —$CX_3$, —$CF_3$, —CN, —OCN, —SCN, —NO, —$NO_2$, =$N_2$, —$N_3$, —$S(O)_2O^-$, —$S(O)_2OH$, —$S(O)_2R^6$, —$OS(O_2)O^-$, —$OS(O)_2OH$, —$OS(O)_2R^6$, —$P(O)(O^-)_2$, —$P(O)(OH)(O^-)$, —$OP(O)_2(O^-)$, —$C(O)R^6$, —$C(S)R^6$, —$C(O)OR^6$, —$C(O)O^-$, —$C(S)OR^6$, and —$C(NR^6)NR^6R^6$, where each X is independently a halogen; each $R^6$ is independently hydrogen, halogen, alkyl, aryl, arylalkyl, arylaryl, arylheteroalkyl, heteroaryl, heteroarylalkyl —$NR^7R^7$, —$C(O)R^7$ or —$S(O)_2R^7$; and each $R^7$ is independently hydrogen, alkyl, alkanyl, alkynyl, aryl, arylalkyl, arylheteralkyl, arylaryl, heteroaryl or heteroarylalkyl.

Reference will now be made in detail to preferred embodiments of the invention. While the invention will be described in conjunction with preferred embodiments, it should be understood that it is not intended to limit the invention to this preferred embodiment. To the contrary, it is intended to cover alternatives, modifications, and equivalents as may be included within the spirit and scope of the invention as defined by the appended claims.

4.2 The Invention

The present invention provides a laspartomycin core peptide, laspartomycin core peptide derivatives, antimicrobial laspartomycin derivatives, methods for making the laspartomycin core peptide, methods for making laspartomycin core peptide derivatives, methods for making antimicrobial laspartomycin derivatives, pharmaceutical compositions of antimicrobial laspartomycin derivatives, methods of inhibiting microbial growth and methods for treating and/or preventing microbial infections in a subject.

Those of skill in the art will appreciate that many of the compounds encompassed by generic formulae (I-III) as well as the compound species specifically described herein, may exhibit the phenomena of tautomerism, conformational isomerism, geometric isomerism and/or stereo isomerism. As the formula drawings within the specification and claims can represent only one of the possible tautomeric, conformational isomeric, enantiomeric or geometric isomeric forms, it should be understood that the invention encompasses any tautomeric, conformational isomeric, enantiomeric and/or geometric isomeric forms of the compounds having one or more of the utilities described herein, as well as mixtures of these various different forms.

4.2.1 —Laspartomycin Core Peptide Derivatives

Laspartomycin core peptide derivatives provide synthetic access to a wide variety of antimicrobial laspartomycin derivatives that may possess greater activity against resistant species than previously described antibiotic agents. The ease with which a wide variety of isolated antimicrobial laspartomycin derivatives may be synthesized from laspartomycin core peptide derivatives may establish a structure-activity relationship for the lipophilic group and/or the linker and linking group. Thus, access to laspartomycin core peptide derivatives may allow for facile investigation of the medicinal chemistry of antimicrobial laspartomycin derivatives.

Laspartomycin core peptide derivatives include compounds described by structural Formula (I):

$$Y^1—L—X^1—N(R^1)—R \quad (I)$$

or a salt or hydrate thereof, wherein either:

(i) $Y^1$—L—$X^1$ taken together is hydrogen; or (ii) $Y^1$ is a linking group;

L is a linker;

$X^1$ is selected from the group consisting of —CO—, —$SO_2$—, —CS—, —PO—, —OPO—, —OC(O)—, —NHCO— and —$NR^1$CO—;

N is nitrogen;

$R^1$ is selected from the group consisting of hydrogen, ($C_1$–$C_{10}$) alkyl optionally substituted with one or more of the same or different $R^2$ groups, ($C_1$–$C_{10}$) heteroalkyl optionally substituted with one or more of the same or different $R^2$ groups, ($C_5$–$C_{10}$) aryl optionally substituted with one or more of the same or different $R^2$ groups, ($C_5$–$C_{15}$) arylaryl optionally substituted with one or more of the same or different $R^2$ groups, ($C_5$–$C_{15}$) biaryl optionally substituted with one or more of the same or different $R^2$ groups, five to ten membered heteroaryl optionally substituted with one or more of the same or different $R^2$ groups, ($C_6$–$C_{16}$) arylalkyl optionally substituted with one or more of the same or different $R^2$ groups and six to sixteen membered heteroarylalkyl optionally substituted with one or more of the same or different $R^2$ groups;

each $R^2$ is independently selected from the group consisting of —$OR^3$, —$SR^3$, —$NR^3R^3$, —CN, —$NO_2$, —$N_3$, —C(O)$OR^3$, —C(O)$NR^3R^3$, —C(S)$NR^3R^3$, —C($NR^3$)$NR^3R^3$, —CHO, $R^3$CO—, —$SO_2R^3$, —$SOR^3$, —PO($OR^3$)$_2$, —PO($OR^3$), —$CO_2$H, —$SO_3$H, —$PO_3$H, halogen and trihalomethyl;

each $R^3$ is independently selected from the group consisting of hydrogen, ($C_1$–$C_6$) alkyl, ($C_5$–$C_{10}$) aryl, 5–10 membered heteroaryl, ($C_6$–$C_{16}$) arylalkyl and six to sixteen membered heteroarylalkyl; and R is the core cyclic peptide of laspartomycin.

Those of skill in the art will appreciate that the compounds of Formula (I) possess the core cyclic peptide of laspartomycin 5 shown below as a common structural motif.

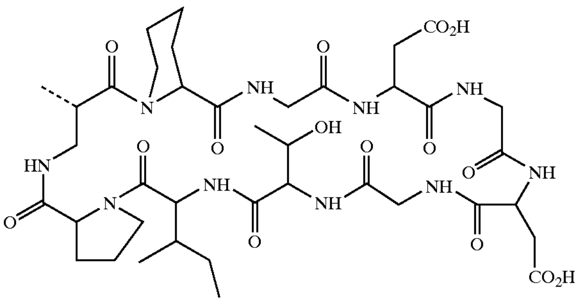

Although the core cyclic peptide R is illustrated as comprised of certain amino acids arranged with a particular connectivity, the specific structure depicted is not intended to be limiting. Thus, it will be understood that the illustrated structure is intended merely as a convenient method for representing the actual compound and to the extent it may be found at a later date that this structural representation of the core cyclic peptide of laspartomycin is incorrect, it is not intended to be limiting in any way.

The moiety covalently bonded to the dashed line of structure 5 which represents the core cyclic peptide R in generic formula I is N($R^1$). Here, N represents nitrogen that is directly attached to the core cyclic peptide R and $R^1$ is a nitrogen substituent.

In a preferred embodiment, $R^1$ is selected from the group consisting of hydrogen, ($C_1$–$C_{10}$) alkyl optionally substituted with one or more of the same or different $R^2$ groups, ($C_1$–$C_{10}$) heteroalkyl optionally substituted with one or more of the same or different $R^2$ groups, ($C_5$–$C_{10}$) aryl optionally substituted with one or more of the same or different $R^2$ groups, ($C_5$–$C_{15}$) biaryl optionally substituted with one or more of the same or different $R^2$ groups, five to ten membered heteroaryl optionally substituted with one or more of the same or different $R^2$ groups, ($C_6$–$C_{16}$) arylalkyl optionally substituted with one or more of the same or different $R^2$ groups and six to sixteen membered heteroarylalkyl optionally substituted with one or more of the same or different $R^2$ groups where $R^2$ is a substituent as defined above in Formula (I). In another preferred embodiment, $R^1$ is selected from the group consisting of hydrogen, ($C_1$–$C_6$) alkyl optionally substituted with one or more of the same or different $R^2$ groups, ($C_3$–$C_7$) alkenyl optionally substituted with one or more of the same or different $R^2$ groups, $C_6$ aryl optionally substituted with one or more of the same or different $R^2$ groups, $C_{12}$ biaryl optionally substituted with one or more of the same or different $R^2$ groups, ($C_6$–$C_{10}$) arylalkyl optionally substituted with one or more of the same or different $R^2$ groups and ($C_6$–$C_{10}$) heteroarylalkyl optionally substituted with one or more of the same or different $R^2$ groups. In yet another preferred embodiment, $R^1$ is selected from the group consisting of hydrogen, methyl, allyl, homoallyl, phenyl, substituted phenyl, benzyl and substituted benzyl. In one particularly preferred embodiment, $R^1$ is hydrogen.

Laspartomycin core peptide derivatives may be H—N($R^1$)—R when $Y^1$—L—$X^1$ taken together are hydrogen. In a preferred embodiment, a laspartomycin core peptide derivative is $H_2N$—R when $R^1$ is hydrogen. Those of skill in the art will appreciate that in this situation the laspartomycin core peptide derivative may be represented by the structural formula 6 shown below, which is identical to the laspartomycin core peptide produced by deacylation of laspartomycin with *Actinoplanes utahensis* (NRRL 12052), supra.

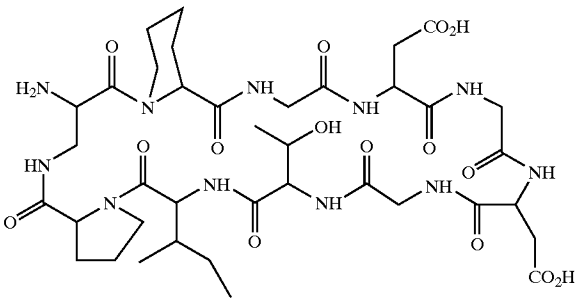

In an alternative embodiment, laspartomycin core peptide derivatives can also be described by the formula $Y^1$—L—$X^1$—N($R^1$)—R. Generally, $X^1$ may be any kind of chemical functionality that can form a covalent bond with nitrogen known to those of skill in the art. In a exemplary embodiment, $X^1$ is selected from the group consisting of —CO—, —$SO_2$—, —CS—, —PO—, —OPO—, —OC(O)—, —NHCO—, —$NR^1$CO—. In another preferable embodiment, $X^1$ is —CO— or —$SO_2$—. In a particularly preferred embodiment, $X^1$ is —CO—.

Connected to $X^1$ in laspartomycin core peptide derivatives of the form $Y^1$—L—$X^1$—N($R^1$)—R is a linking moiety of the formula $Y^1$—L, where L is a linker and $Y^1$ is a linking group. The nature of linker L and linking group $Y^1$ may vary extensively. The linker L may be hydrophilic or hydrophobic, long or short, rigid, semirigid or flexible.

A wide variety of linkers L comprised of stable bonds suitable for spacing linking groups such as $Y^1$ from the core cyclic peptide are known in the art, and include by way of example and not limitation, alkyl, heteroalkyl, acyclic heteroatomic bridges, aryl, arylaryl, arylalkyl, heteroaryl, heteroaryl-heteroaryl, substituted heteroaryl-heteroaryl, heteroarylalkyl, heteroaryl-heteroalkyl and the like. Thus, linker L may include single, double, triple or aromatic carbon-carbon bonds, nitrogen-nitrogen bonds, carbon-nitrogen, carbon-oxygen bonds and/or carbon-sulfur bonds, and may therefor include functionalities such as carbonyls, ethers, thioethers, carboxamides, sulfonamides, ureas, urethanes, hydrazines, etc.

Choosing a suitable linker is within the capabilities of those having skill in the art. For example, where a rigid linker is desired, L may be a rigid polyunsaturated alkyl or an aryl, biaryl, heteroaryl etc. Where a flexible linker is desired, L may be a flexible peptide such as Gly-Gly-Gly or a flexible saturated alkanyl or heteroalkanyl. Hydrophilic linkers may be, for example, polyalcohols or polyethers such as polyalkyleneglycols. Hydrophobic linkers may be, for example, alkyls or aryls.

Preferably, linking group $Y^1$ is capable of mediating formation of a covalent bond with complementary reactive functionality of a lipophilic group to provide an isolated antimicrobial laspartomycin derivative. Accordingly, linking group $Y^1$ may be any reactive functional group known to those of skill in the art. $Y^1$ may be for example, a photochemically activated group, an electrochemically activated group, a free radical donor, a free radical acceptor, a nucleophilic group or an electrophilic group. However, those of skill in the art will recognize that a variety of functional groups which are typically unreactive under certain reaction conditions can be activated to become reactive. Groups that can be activated to become reactive include, e.g., alcohols, carboxylic acids and esters, including salts thereof.

Thus, in a preferred embodiment, $Y^1$ is selected from the group consisting of —$NHR^1$, —$NH_2$, —OH, —SH, —PH, halogen, —CHO, —$R^1$CO, —$SO_2$H, —$PO_2$H, —$N_3$, —CN, —$CO_2$H, —$SO_3$H, —$PO_3$H, —$PO_2$($OR^1$)H, —$CO_2R^1$, —$SO_3R^1$ and —PO($OR^1$)$_2$. In another preferred embodiment, $Y^1$ is selected from the group consisting of —$NHR^1$, —$NH_2$, —OH, —SH, —CHO, —$CO_2$H, $R^1$CO— and —$CO_2R^1$. In a particularly preferred embodiment, $Y^1$ is selected from the group consisting of —SH, —$NH_2$, —OH, —$CO_2$H, and —$CO_2R^1$.

Some embodiments of $Y^1$—L include for example, compounds where L is —$(CH_2)_n$—, n is an integer between 1 and 8, $Y^1$ is selected from the group consisting of —$NH_2$, —OH, —$CO_2$H, and —$CO_2R^1$ and the corresponding analogues where any suitable hydrogen is substituted. Other embodiments of $Y^1$—L include any amino acid, which may be for example, a D or L α-amino acid, a β-amino acid or a γ-amino acid. Thus, $Y^1$—L may be a dipeptide, a tripeptide or a tetrapeptide comprised of any combination of amino acids (preferably α-amino acids). The polarity of the peptide bond in these peptides may be either C→N or N→C.

In a preferred embodiment of the laspartomycin core peptide derivative, $R^1$ is hydrogen, $Y^1$ is selected from the group consisting $H_2N$—, —OH, —SH, —$CO_2$H, —$CO_2$R, $X^1$ is —CO— and L is selected from the group consisting of:

(L1)

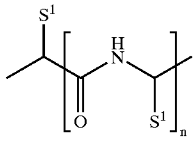

(L2)

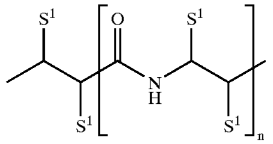

(L3)

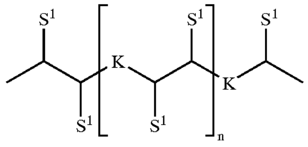

-continued (L4)

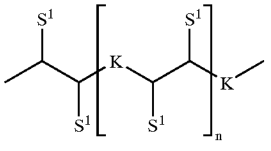

or a salt or hydrate thereof, wherein:

n is 0, 1, 2 or 3;

each $S^1$ is selected from the group consisting of hydrogen, ($C_1$–$C_{10}$) alkyl optionally substituted with one or more of the same or different $R^4$ groups, ($C_1$–$C_{10}$) heteroalkyl optionally substituted with one or more of the same or different $R^4$ groups, ($C_5$–$C_{10}$) aryl optionally substituted with one or more of the same or different $R^4$ groups, ($C_5$–$C_{15}$) arylaryl optionally substituted with one or more of the same or different $R^4$ groups, ($C_5$–$C_{15}$) biaryl optionally substituted with one or more of the same or different $R^4$ groups, five to ten membered heteroaryl optionally substituted with one or more of the same or different $R^4$ groups, ($C_6$–$C_{16}$) arylalkyl optionally substituted with one or more of the same or different $R^4$ groups and six to sixteen membered heteroarylalkyl optionally substituted with one or more of the same or different $R^4$ groups;

each $R^4$ is independently selected from the group consisting of —$OR^5$, —$SR^5$, —$NR^5R^5$, —CN, —$NO_2$, —$N_3$, —$C(O)OR^5$, —$C(O)NR^5R^5$, —$C(S)NR^5R^5$, —$C(NR^5)NR^5R^5$, —CHO, —$R^5CO$, —$SO_2R^5$, —$SOR^5$, —$PO(OR^5)_2$, —$PO(OR^5)$, —$CO_2H$, —$SO_3H$, —$PO_3H$, halogen and trihalomethyl;

each $R^5$ is independently selected from the group consisting of hydrogen, ($C_1$–$C_6$) alkyl, ($C_5$–$C_{10}$) aryl, 5–10 membered heteroaryl, ($C_6$–$C_{16}$) arylalkyl and six to sixteen membered heteroarylalkyl; and each K is independently selected from the group consisting of oxygen, nitrogen, sulfur and phosphorus.

In a preferred embodiment, $S^1$ is a side chain of a genetically encoded a amino acid. Exemplary preferred embodiments of $Y^1$—L—$X^1$—NH—R where K is independently selected from the group consisting of oxygen, nitrogen and sulfur include the following compounds:

8

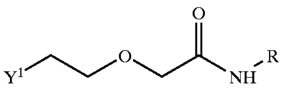

10

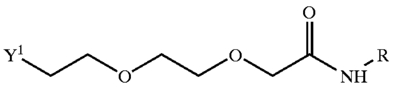

12

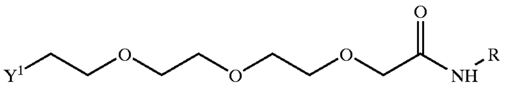

14

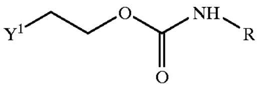

-continued

16

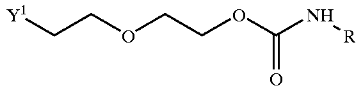

18

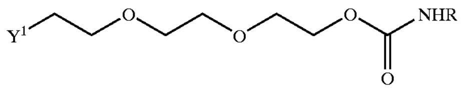

20

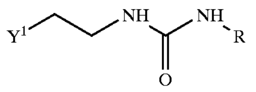

22

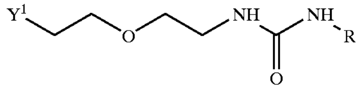

24

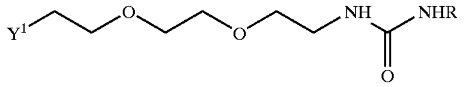

Preferably, in the above illustrated embodiments, $Y^1$ is selected from the group consisting of —SH, —$NH_2$ or —OH. More preferably $Y^1$ is —OH.

In another preferred embodiment of the laspartomycin core peptide derivative, $R^1$ is hydrogen, $Y^1$ is $H_2N$—, $X^1$ is —CO—, n is as previously defined, each $S^1$ is independently as previously defined and L is L1 as previously defined. Preferably, in this embodiment, each $S^1$ is independently a side-chain of a genetically encoded α-amino acid. More preferably, each $S^1$ is independently a side-chain of glycine, asparagine, aspartic acid, glutamine, glutamic acid, tryptophan, phenylalanine, tyrosine, leucine, alanine, isoluecine and valine. Exemplary preferred embodiments of $Y^1$—L—$X^1$—N(H)—R where each $S^1$ is independently a side-chain of glycine, asparagine, aspartic acid, glutamine, glutamic acid and tryptophan include the following compounds where R and $Y^1$ are as previously defined:

26

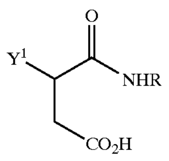

28

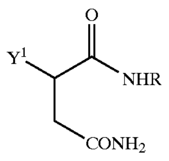

30

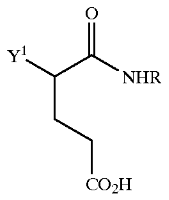

-continued

32

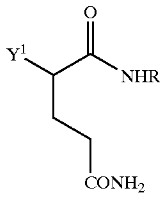

34

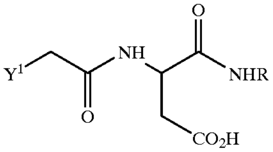

36

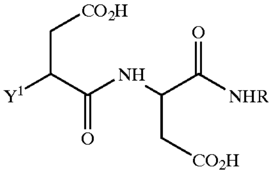

38

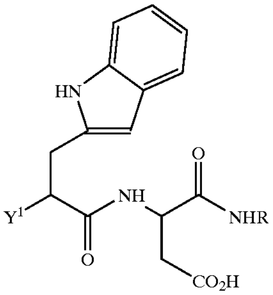

40

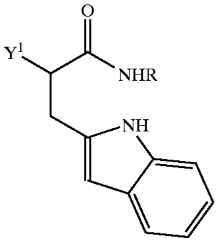

42

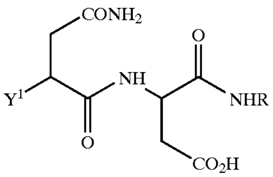

44

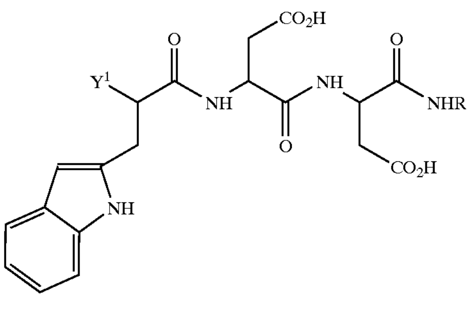

-continued

46

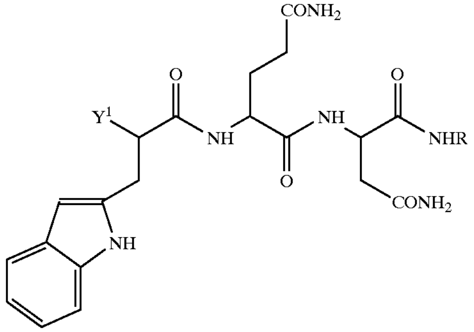

48

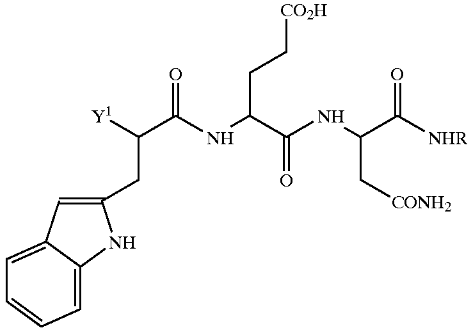

50

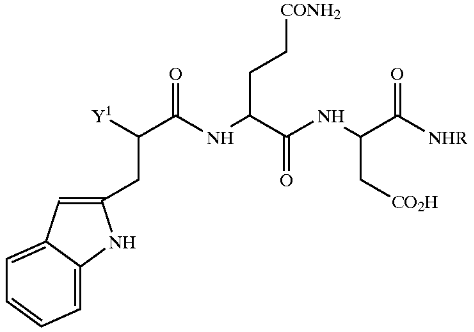

Preferably, $Y^1$ is selected from the group consisting of —OH, —SH and —$NHR^1$ and —$NH_2$. Most preferably, $Y^1$ is —$NH_2$ and the a amino acids illustrated have the L stereochemistry.

4.2.2 Methods of Making the Laspartomycin Core Peptide

The present invention provides methods for making a laspartomycin core peptide that includes culturing the microorganism *Streptomyces viridochromogenes*, ssp. *komabensis* (ATCC 29814) in a culture medium to provide laspartomycin. Isolation of laspartomycin followed by cleavage of a lipophilic fragment provides the laspartomycin core peptide.

Parent cultures of *Streptomyces viridochromogenes*, ssp. *komabensis* (ATCC 29814) especially suitable for biochemical synthesis of laspartomycin may be selected by conventional methods known to those of skill in the art. A preferred method for selecting a parent culture which provides improved yields of laspartomycin is described in Example 1.

Growing inocula and inoculating culturing medium are also well known to those of skill in the art and exemplary methods for *Streptomyces viridochromogenes*, ssp. *komabensis* are described in Umezawa et al., U.S. Pat. No. 3,639,582, which is herein incorporated by reference, and Example 2.

Generally, any culturing medium which supports *Streptomyces viridochromogenes*, ssp. *komabensis* growth may be used in the biochemical synthesis of laspartomycin and selection of such medium is within the capability of those of skill in the art. Representative examples of culturing media which supports *Streptomyces viridochromogenes*, ssp. *komabensis* growth may be found in Umezawa et al., U.S. Pat. No. 3,639,582 and Examples 3 and 4.

Preferred media, times, temperatures and pH for culturing *Streptomyces viridochromogenes*, ssp. *komabensis* that provide good yields of laspartomycin are described in Umezawa et al., U.S. Pat. No. 3,639,582 and Examples 3 and 4. It should be noted that the choice of culturing medium and the quantitative ratio of its constituents directly affects the ratio of the different lipopeptides that comprise laspartomycin.

Generally, laspartomycin may be purified and isolated by any art-known techniques such as high performance liquid chromatography, counter current extraction, centrifugation, filtration, precipitation, ion exchange chromatography, gel electrophoresis, affinity chromatography and the like. The actual conditions used to purify laspartomycin will depend, in part, on factors such as net charge, hydrophobicity, hydrophilicity, etc., and will be apparent to those having skill in the art.

Preferably, laspartomycin is isolated from the culture medium by extractive procedures. In one preferred embodiment (see e.g., Example 5), the fermentation broth containing laspartomycin is mixed with organic solvent (preferably 1-butanol). While not wishing to be bound by theory, the anionic form of laspartomycin may form a chelate with divalent metal ion that is soluble in organic solvent. The organic phase containing laspartomycin is then combined with an aqueous acid solution at a pH less than about 3.0 (most preferably at a pH of about 2.0). While not wishing to be bound by theory, protonation of the anion of laspartomycin may disrupt the divalent metal chelate form.

More preferably, (see e.g., Example 6), the fermentation broth containing laspartomycin is acidified to a pH of at least about 3.0 (more preferably to a pH of about 2.0). The cells and any precipitate may then be separated by any conventional method known to those of skill in the art and suspended in water. The pH of the aqueous suspension is adjusted to at least about pH 7.0, a divalent metal ion is added and the pH of the aqueous suspension is adjusted to about 8.0 to about 9.0. Preferably the concentration of divalent metal ion in the aqueous suspension is between about 4 mmol/l and about 10 mmol/l. In one embodiment, the divalent metal ion is selected from the group consisting of calcium, magnesium and zinc. Most preferably, the divalent metal ion is calcium. The aqueous suspension is then extracted with organic solvent (preferably, 1-butanol). The organic phase containing laspartomycin is then combined with an aqueous acid solution at a pH less than about 3.0 (most preferably at a pH of about 2.0).

Henceforth, in either of the above preferred embodiments, laspartomycin may be partitioned between organic solvent and aqueous solution by conventional methods known to those of skill in the art. Thus, for example, when the organic solvent solution of laspartomycin is treated with a neutral or basic aqueous solution, laspartomycin may be extracted into aqueous solution. Acidification of the aqueous solution of laspartomycin enables extraction of laspartomycin into organic solvent. Preferably, laspartomycin is partitioned between organic solvent and aqueous solution at least twice. Laspartomycin may be isolated as either the free acid (see e.g. Example 7) or a metal salt (see e.g., Examples 5 and 6) using conventional methods known to those of skill in the art.

Generally, the lipophilic moiety of laspartomycin may be cleaved with an enzyme to provide the laspartomycin core peptide. It should be noted that addition of an appropriate enzyme to the culture medium may provide the laspartomycin core peptide directly, thus obviating the need to isolate laspartomycin. Preferably, however, isolated laspartomycin is treated with an enzyme which may be selected by those of skill in the art. The enzyme may be, for example, a degradative enzyme such as a peptidase, esterase or thiolase, of which numerous examples exist in the art. Preferably, the enzyme is a deacylase.

In an exemplary embodiment, the cleavage step involves culturing a microorganism that can produce a deacylase in an appropriate culture medium and contacting laspartomycin with the culture medium containing the deacylase. Microorganisms that produce deacylases are well known to those of skill in the art. In a preferred embodiment, the microorganism *Actinoplanes utahensis* (NRRL 12052) provides a deacylase.

Parent cultures of *Actinoplanes utahensis* (NRRL 12052) especially suitable for cleaving the lipophilic fragment of laspartomycin may be selected by methods known to those of skill in the art. A preferred method for selecting a parent culture which provides improved yields of laspartomycin core peptide is described in Example 8.

Growing inocula and inoculating culturing medium are also well known to those of skill in the art and exemplary methods for *Actinoplanes utahensis* (NRRL 12052) are described in Boeck et al., 1988, *J. Antibiot.*, 41, 1085 and Debono et. al., 1988, *J. Antibiotics*, 41, 1093 which are herein incorporated by reference and Example 8.

Any culturing medium which supports *Actinoplanes utahensis* (NRRL 12052) growth may be used and selection of such medium is within the capability of those of skill in the art. Representative examples of culturing medium which supports *Actinoplanes utahensis* (NRRL 12052) growth may be found in Boeck et al., 1988, *J. Antibiot.*, 41, 1085, Debono et. al., 1988, *J. Antibiotics*, 41, 1093 and Example 8.

Preferred media, times, temperatures and pH for culturing *Actinoplanes utahensis* (NRRL 12052) that provide good yields of the deacylase are described in Boeck et al., 1988, *J. Antibiot.*, 41, 1085, Debono et. al., 1988, *J. Antibiotics*, 41, 1093 and Example 8.

In a preferred embodiment, laspartomycin is contacted with a culture medium containing *Actinoplanes utahensis* (NRRL 12052) for about 16 hours at about 29° C. to provide the laspartomycin core peptide having the structure:

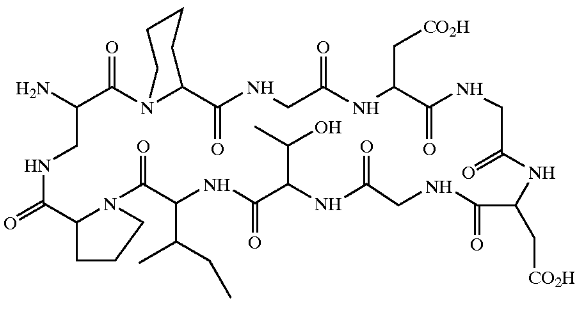

It should be noted that contacting laspartomycin with a culture medium containing *Actinoplanes utahensis* (NRRL 12052) for about 4 hours at about 29° C. (see e.g., Example 10) provides material enriched in the laspartomycin core peptide having the structure:

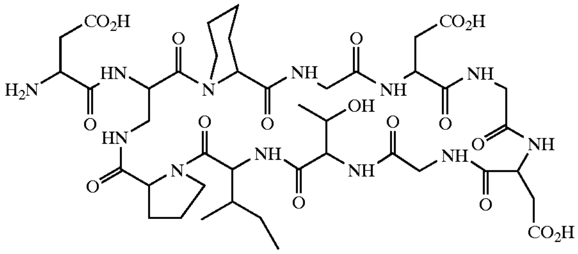

While not wishing to be bound by theory, the deacylase produced by *Actinoplanes utahensis* (NRRL 12052) may be an exopeptidase that first cleaves the lipophilic fragment of laspartomycin to provide 54. The exocyclic aspartic acid residue of 54 is then hydrolyzed by extended treatment with deacylase or proteases to provide compound 6.

The laspartomycin core peptide may be purified and isolated by any art-known techniques such as high performance liquid chromatography, counter current extraction, centrifugation, filtration, precipitation, ion exchange chromatography, gel electrophoresis, affinity chromatography and the like. The actual conditions used to purify the laspartomycin core peptide will depend, in part, on factors such as net charge, hydrophobicity, hydrophilicity, etc., and will be apparent to those having skill in the art. Preferably, the laspartomycin core peptide is isolated by centrifugation and chromatography on reverse phase resin (See e.g., Examples 9 and 10).

4.2.3 Methods of Making Laspartomycin Core Peptide Derivatives

Laspartomycin core peptide derivatives may be made starting from laspartomycin core peptide 6 or laspartomycin core peptide 54. Typically, either 6 or 54 will be produced by deacylation of laspartomycin provided by culturing *Streptomyces viridochromogenes*, ssp. *komabensis* (ATCC 29814). However, it may be possible to synthesize either 6 or 54 using methods known in the art for synthesizing cyclic peptides. For example, linear peptides may be prepared using solution phase or solid phase peptide synthesis and then cyclized. Preferably, laspartomycin core peptide 6 will be used as a starting material for the synthesis of laspartomycin core peptide derivatives. Those of skill in the art will realize that any of the methods presented below can also be used to prepare laspartomycin core peptide derivatives from intermediate 54.

Starting materials useful for preparing laspartomycin core peptide derivatives from the laspartomycin core peptide 6 and intermediates thereof are either commercially available or may be prepared by conventional synthetic methods. A number of general synthetic approaches may be envisioned for converting cyclic peptide 6 to laspartomycin core peptide derivatives. These include but are not limited to the approaches outlined in Schemes I–III.

$Y^1$—L—$X^{1'}$+NH($R^1$)—R→$Y^1$—L—$X^1$N($R^1$)—R    Scheme 1

In Scheme 1, $X^{1'}$ may be an activated derivative of $X^1$ such as for example, —CO—Z, —OCO—Z, —$SO_2$—Z, —CS—Z, —PO—Z, —OPO—Z—, —OC(O)—Z, —NHCO—Z or —$NR^1$CO—Z where Z is a leaving group such as halogen or an activated ester. Methods for making activated derivatives of $X^1$ and for reacting these derivatives with either primary or secondary amines to form the $X^1$—N covalent bond are known to those of skill in the art and may be found in any compendium of standard synthetic methods (See e.g., March, J., *Advanced Organic Chemistry; Reactions, Mechanisms and Structure*, $4^{th}$ ed., 1992; Larock, R., *Comprehensive Organic Transformations*, VCH: New York, 1999; Bodanzsky, M., *Principles of Peptide Synthesis*; Springer Verlag, 1984; Bodanzsky, M., *Practice of Peptide Synthesis*; Springer Verlag, 1984). Other synthetic methods based on free radical chemistry, photochemistry or electrochemistry for forming the $X^1$—N bond will be apparent to those of skill in the art.

Those of skill in the art will appreciate that protection of either $Y^1$ and/or L may be necessary to make activated derivatives of $X^1$ for formation of the $X^1$—N bond. In the event that protection of either $Y^1$ and/or L is necessary to form the $X^1$—N linkage, then deprotection of either $Y^1$ and/or L will be necessary to provide the desired laspartomycin core peptide derivative. Methods for protection and deprotection of common organic functionalities are known to those of skill in the art and may be used as necessary in the synthesis of laspartomycin core peptide derivatives (see e.g. Greene, T. W., *Protective Groups in Organic Synthesis*, $3^{rd}$ edition, 1999).

$Y^1$—$L^3$+$L^2$—$X^1$—N($R^1$)R→$Y^1$—L—$X^1$N($R^1$)—R    Scheme 2

Scheme 2 describes a convergent approach where $Y^1$—L—$X^1$N($R^1$)—R is synthesized by combining two molecules ($Y^1$—$L^3$ and $L^2$—$X^1$—N($R^1$)R) to form the laspartomycin core peptide derivative. Here $L^3$ and $L^2$ are fragments which, when covalently linked, form the linker L. Such approaches may be particularly useful when L is an oligomer such as a polyamide or poylether. Methods for combining oligomeric subunits such as ether or amide monomers, dimers etc. are known to those of skill in the art. Fragments such as $Y^1$—$L^3$ and $L^2$—$X^{1'}$ (useful in forming the $X^1$—N bond as described above) are either commercially available or may be made by standard synthetic methods.

$Y^x$—L—$X^1$N($R^1$)—R→$Y^1$—L—$X^1$N($R^1$)—R    Scheme 3

Finally, simple functional group interchange may be used to prepare $Y^1$—L—$X^1$N($R^1$)—R from $Y^x$—L—$X^1$N($R^1$)—R. Here, $Y^x$ is a functional group that may be converted to $Y^1$. Many methods for effecting functional group interchange are known to those of skill in organic synthesis (See e.g., March, J., *Advanced Organic Chemistry; Reactions, Mechanisms and Structure*, $4^{th}$ ed., 1992; Larock, R., *Comprehensive Organic Transformations*, VCH: New York, 1999).

4.2.4 The Antimicrobial Laspartomycin Derivatives

The antimicrobial laspartomycin derivatives of the present invention offer some significant advantages over traditional antibiotics. The antimicrobial laspartomycin derivatives are generally active against many gram positive bacteria. More importantly, the antimicrobial laspartomycin derivatives of the present invention may be effective against methicillin resistant bacteria and/or strains resistant to vancomycin. Thus, the antimicrobial laspartomycin derivatives may inhibit or prevent growth of a number of microbes generally resistant to known antibiotics.

Antimicrobial laspartomycin derivatives include compounds described by structural Formula (II):

$Y^2$—($X^2$—$X^3$)—(L)—($X^1$)—N($R^1$)—R    (II)

or an pharmaceutically acceptable salt or hydrate thereof, wherein:

$Y^2$ is a lipophilic group;

$X^2$ is a linked group;

$X^3$ is a linked group; and $X^1$, L, N, $R^1$ and R are as defined for Formula (I) in Section 4.2.1 of this Application.

Connected to $X^1$ in isolated antimicrobial laspartomycin derivatives of Formula (II) is a linking moiety of the formula ($X^2$—$X^3$) where L is a linker and $X^2$ and $X^3$ are linked groups that attach a lipophilic molecule $Y^2$ to the linker L. The nature of linker L and the linked groups $X^2$ and $X^3$ may vary extensively. The linker L has been described and defined in Section 4.2.1 of this Application.

As will be appreciated by those having skill in the art, a linking moiety such as ($X^2$—$X^3$) will typically be at least bifuictional. Thus, they will have at least one functional group or moiety capable of forming a linkage with the linker and at least one functional group or moiety capable of forming a linkage with a lipophilic group.

Preferably, linking moiety ($X^2$—$X^3$) taken together is a covalent linkage. In this preferred embodiment, linking moiety ($X^2$—$X^3$) is any covalent linkage that may be formed by any method known to those of skill in the art. Thus, for example, linking moiety ($X^2$—$X^3$) may be any single, double or triple bond that can be formed between two carbon atoms, a carbon atom and a heteroatom or two heteroatoms. For example, ($X^2$—$X^3$) include linkages such as $—CH_2—CH_2—$, —CH=CH—, —C=CH—, —CH=CH—, —C≡C—, $—NH—CH_2—$, —N=CH—, $—CH_2—NH—$, —CH=N—, —NH—NH—, —N=N—, —S—S—, —O—O—, —Se—Se—, $—S—CH_2—$, $—CH_2—S—$, $—O—CH_2—$, $—CH_2—O—$, $—Se—CH_2—$, $—CH_2—Se—$, —NH—S—, —P—N—, —N—O— and the corresponding substituted analogs where any suitable hydrogen is substituted with the same or different substituent.

Preferably, ($X^2$—$X^3$) taken together are selected from the group consisting of —C(O)O—, —O(O)C—, —CONH—, —NHCO—, $—CONR^1—$, $—NR^1CO—$, —C(O)S—, —S(O)C—, $—OSO_2—$, $—S(O_2)O—$, $—NHSO_2—$, $—NR^1SO_2—$, $—S(O_2)NH—$, $—S(O_2)NR^1—$, —C(S)NH—, —NHC(S)—, —NHP(O)—, —P(O)NH—, OP(O)—, —P(O)O—, SP(O)—, —P(O)S—, —OC(O)NH—, —NHC(O)O—, $—OC(O)NR^1—$, $—NR^1C(O)O—$, —OC(O)O—, —NHC(O)NH—, $—NHC(O)NR^1—$, $—NR^1C(O)NH—$ and $—NR^1C(O)NR^1$ and the corresponding substituted analogs where any suitable hydrogen is substituted with the same or different substituent. In a preferred embodiment, ($X^2$—$X^3$) taken together are selected from the group consisting of —C(O)O—, —O(O)C—, CONH—, —NHCO—, $—CONR^1—$, $—NR^1CO—$, —C(O)S—, —S(O)C—, $—NHSO_2—$, $—NR^1SO_2$, $—S(O_2)NH—$, $—S(O_2)NR^1—$, C(S)NH—, —NHC(S)—, —OC(O)NH—, —NHC(O)O—, $—OC(O)NR^1—$, $—NR^1C(O)O—$ and —OC(O)O— and the corresponding substituted analogs where any suitable hydrogen is substituted with the same or different substituent. In another preferred embodiment, ($X^2$—$X^3$) taken together are selected from the group consisting of —C(O)O—, —O(O)C—, —CONH—, —NHCO—, $—CONR^1—$, $—NR^1CO—$, $—NHSO_2—$, $—NR^1SO_2$, $—S(O_2)NH—$, $—S(O_2)NR^1—$, —OC(O)NH—, —NHC(O)O—, $—OC(O)NR^1—$ and $—NR^1C(O)O—$ and the corresponding substituted analogs where any suitable hydrogen is substituted with the same or different substituent.

Some embodiments of the linking moiety ($X^2$—$X^3$) combined with linker L include partial structures such as $—(X^2—X^3)\text{-}(CH_2)_n—$, where n is between 1 and 8, ($X^2$—$X^3$) taken together are selected from the group consisting of —C(O)O—, —O(O)C—, —CONH—, —NHCO—, $—CONR^1—$, $—NR^1CO—$, $—NHSO_2—$, $—NR^1SO_2$, $—S(O_2)NH—$, $—S(O_2)NR^1—$, —OC(O)NH—, —NHC(O)O—, $—OC(O)NR^1—$ and $—NR^1C(O)O—$ and the corresponding analogues where any suitable hydrogen is substituted. Other embodiments of the linking moiety ($X^2$—$X^3$) combined with linker L include representations where $X^3$—L taken together are derived from any amino acid, which may be for example, a D or L α-amino acid, a β-amino acid and a γ-amino acid and $X^2$, for example is —CO— or $—SO_2—$. Taken together $X^3$—L also may also be a dipeptide, a tripeptide or a tetrapeptide derivative comprised of any combination of amino acids. The polarity of the peptide bond in these peptides may be either C→N or N→C.

Generally, the lipophilic group $Y^2$ will be hydrophobic and when substituted will be substituted with hydrophobic substituents. Those of skill in the art will appreciate that the size and/or length of the lipophilic group will depend, in part, on the nature of fragments such as L, ($X^2$—$X^3$), $X^1$ and $R^1$ that comprise the antimicrobial laspartomycin derivatives.

In a preferred embodiment, the lipophilic group $Y^2$ is selected from the group consisting of ($C_6$–$C_{25}$) alkyl optionally substituted with one or more of the same or different $R^2$ groups, ($C_6$–$C_{25}$) heteroalkyl optionally substituted with one or more of the same or different $R^2$ groups, ($C_8$–$C_{25}$) aryl optionally substituted with one or more of the same or different $R^2$ groups, ($C_8$–$C_{25}$) arylaryl optionally substituted with one or more of the same or different $R^2$ groups, ($C_8$–$C_{25}$) biaryl optionally substituted with one or more of the same or different $R^2$ groups, eight to twenty five membered heteroaryl optionally substituted with one or more of the same or different $R^2$ groups, ($C_8$–$C_{25}$) arylalkyl optionally substituted with one or more of the same or different $R^2$ groups and eight to twenty five membered heteroarylalkyl optionally substituted with one or more of the same or different $R^2$ groups;

each $R^2$ is independently selected from the group consisting of $—OR^3$, $—SR^3$, $—NR^3R^3$, —CN, $—NO_2$, $—N_3$, $—C(O)OR^3$, $—C(O)NR^3R^3$, $—C(S)NR^3R^3$, $—C(NR^3)NR^3R^3$, —CHO, $—R^3CO$, $—SO_2R^3$, $—SOR^3$, $—PO(OR^3)_2$, $—PO(OR^3)$, $—CO_2H$, $—SO_3H$, $—PO_3H$, halogen and trihalomethyl;

each $R^3$ is independently selected from the group consisting of hydrogen, ($C_1$–$C_6$) alkyl, ($C_5$–$C_{10}$) aryl, 5–10 membered heteroaryl, ($C_6$–$C_{16}$) arylalkyl and 6–16 membered heteroarylalkyl.

In a more preferred embodiment, the lipophilic group $Y^2$ is selected from the group consisting of ($C_8$–$C_{20}$) alkyl optionally substituted with one or more of the same or different $R^2$ groups, ($C_8$–$C_{20}$) heteroalkyl optionally substituted with one or more of the same or different $R^2$ groups, ($C_8$–$C_{20}$) aryl optionally substituted with one or more of the same or different $R^2$ groups, ($C_8$–$C_{20}$) arylaryl optionally substituted with one or more of the same or different $R^2$ groups, ($C_8$–$C_{20}$) biaryl optionally substituted with one or more of the same or different $R^2$ groups, eight to twenty membered heteroaryl optionally substituted with one or more of the same or different $R^2$ groups, ($C_8$–$C_{20}$) arylalkyl optionally substituted with one or more of the same or different $R^2$ groups and eight to twenty membered heteroarylalkyl optionally substituted with one or more of the same or different $R^2$ groups where $R^2$ is as defined above.

In one preferred embodiment, the lipophilic group $Y^2$ is selected from the group consisting of ($C_8$–$C_{20}$) alkyl optionally substituted with one or more of the same or different $R^2$ groups, ($C_8$–$C_{20}$) heteroalkyl optionally substituted with one or more of the same or different $R^2$ groups, ($C_8$–$C_{20}$) aryl optionally substituted with one or more of the same or different $R^2$ groups, $(C_8-C_{20})$ arylaryl optionally substituted with one or more of the same or different $R^2$ groups, $(C_8-C_{20})$ biaryl optionally substituted with one or more of the same or different $R^2$ groups, ten to twenty membered heteroaryl optionally substituted with one or more of the same or different $R^2$ groups, $(C_8-C_{20})$ arylalkyl optionally substituted with one or more of the same or different $R^2$ groups and ten to twenty membered heteroarylalkyl optionally substituted with one or more of the same or different $R^2$ groups. In another preferable embodiment, the lipophilic group $Y^2$ is selected from the group consisting of $(C_8-C_{20})$ alkyl optionally substituted with one or more of the same or different $R^2$ groups. In yet another preferable embodiment, the lipophilic group $Y^2$ is selected from the group consisting of $(C_{10}-C_{16})$ alkyl optionally substituted with one or more of the same or different $R^2$ groups.

In an exemplary embodiment of the isolated antimicrobial laspartomycin derivative of Formula (II), $X^1$ is —CO— or —$SO_2$—, ($X^2$—$X^3$) taken together are selected from the group consisting of —C(O)O—, —O(O)C—, —CONH—, —NHCO—, —C(O)S—, —S(O)C—, —$OSO_2$—, —$S(O_2)$O—, —$NHSO_2$—, —$S(O_2)$NH—, —C(S)NH—, —NHC(S)—, —NHP(O)—, —P(O)NH—, OP(O)—, —P(O)O—, —SP(O)—, —P(O)S—, —OC(O)NH—, —NHC(O)O—, —OC(O)$NR^1$—, —$NR^1$C(O)O—, —OC(O)O—, —NHC(O)NH—, —NHC(O)$NR^1$— and —$NR^1$C(O)O—, $R^1$ is hydrogen and L is selected from the group consisting of L1, L2, L3 and L4 where L1, L2, L3 and L4 are as defined in Section 4.2.1 of this Application In a preferred embodiment, $S^1$ is a side chain of a genetically encoded α amino acid. Exemplary preferred embodiments of $Y^2$—($X^2$—$X^3$)—L—$X^1$—N($R^1$)—R where K is independently selected from the group consisting of oxygen, nitrogen and sulfur include the following compounds where $Y^2$, $X^2$, $X^3$ and R are as previously defined:

54

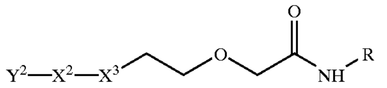

56

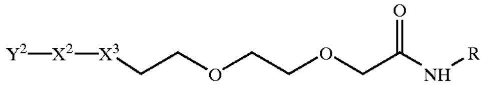

58

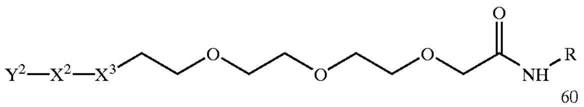

60

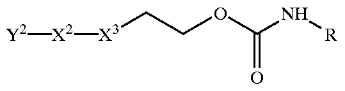

62

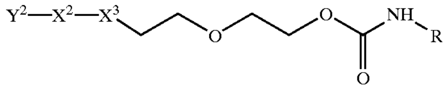

64

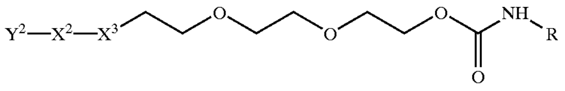

-continued

66

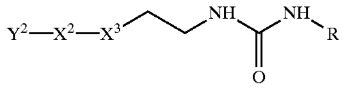

68

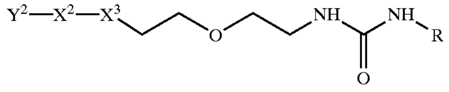

70

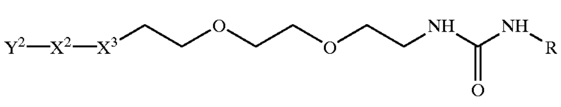

Preferably, in the these embodiments, $X^3$ is selected from the group consisting of —S—, —O— or —NH— and $X^2$ is selected from the group consisting of —CO—, —$SO_2$—, —OC(O)—, —NHC(O)— and —$NR^1$C(O)—. In an alternative embodiment, $X^2$ is selected from the group consisting of —S—, —O— or —NH— and $X^3$ is selected from the group consisting of —CO—, —$SO_2$—, —OC(O)—, —NHC(O)— and —$NR^1$C(O)—.

In another preferred embodiment of the antimicrobial laspartomycin derivatives, $X^1$ is —CO— or —$SO_2$—, ($X^2$—$X^3$) taken together are selected from the group consisting of —CONH—, —$S(O_2)$NH—, —C(S)NH—, —P(O)NH—, —OC(O)NH—, —OC(O)$NR^1$—, —NHC(O)NH—, and —NHC(O)$NR^1$, $R^1$ is hydrogen, n is as defined in Section 4.2.1 of this Application and L is L1 as defined in Section 4.2.1 of this Application. Preferably, in this embodiment, each $S^1$ is independently a side-chain of a genetically encoded α-amino acid. More preferably, each $S^1$ is independently a side-chain of glycine asparagine, aspartic acid, glutamine, glutamic acid, tryptophan, phenylalanine, tyrosine, leucine, alanine, isoluecine and valine. Exemplary preferred embodiments of $Y^2$—($X^2$—$X^3$)—L—$X^1$—N($R^1$)—R where each $S^1$ is independently a side-chain of glycine asparagine, aspartic acid, glutamine, glutamic acid and tryptophan include the following compounds where $Y^2$, ($X^2$—$X^3$) taken together and R are as previously defined:

72

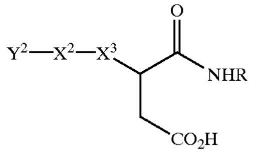

74

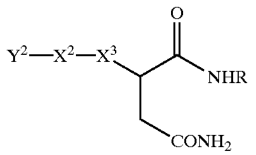

76

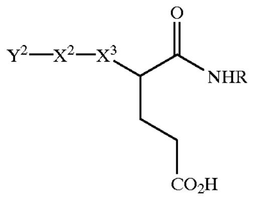

-continued

78

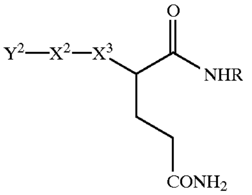

80

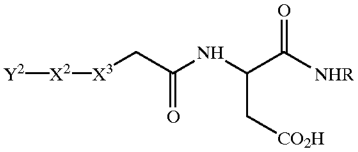

82

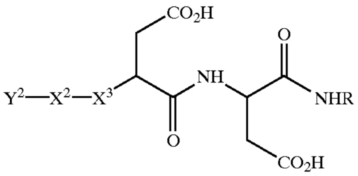

84

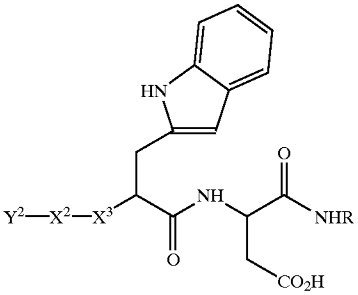

86

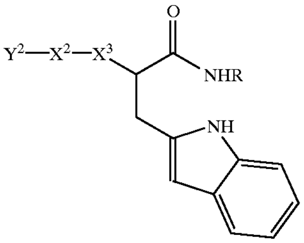

88

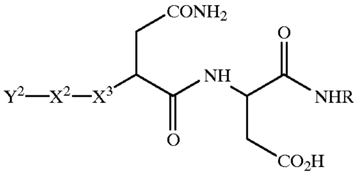

90

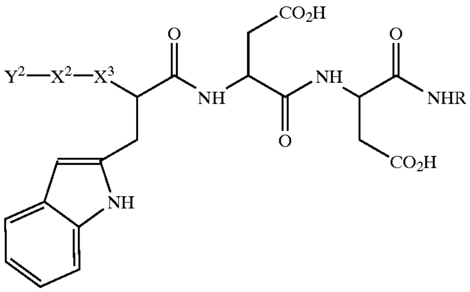

-continued

92

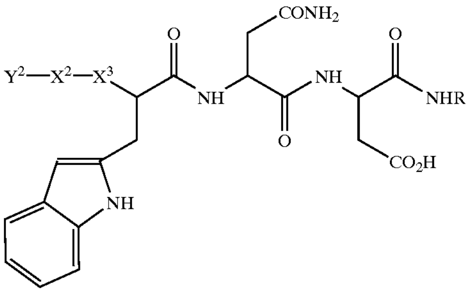

96

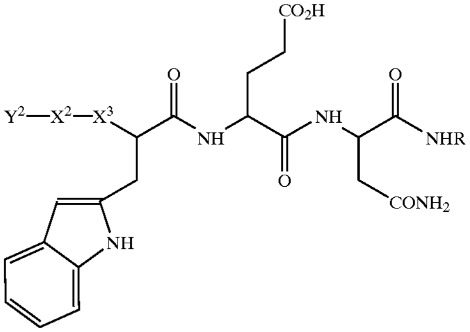

98

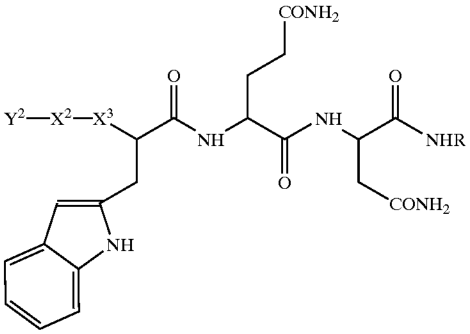

Preferably, in the these embodiments $X^3$ is selected from the group consisting of —S—, —O— or —NH— and $X^2$ is selected from the group consisting of —CO—, —$SO_2$—, —OC(O)—, —NHC(O)— and —$NR^1C(O)$—. In alternative embodiment, $X^2$ is selected from the group consisting of —S—, —O— or —NH— and $X^3$ is selected from the group consisting of —CO—, —$SO_2$—, —OC(O)—, —NHC(O)— and —$NR^1C(O)$—. Preferably, in the above depicted embodiments the illustrated a amino acids have the L stereochemistry.

In a preferred embodiment $X^2$—$X^3$ taken together are —CONH— or —$SO_2NH$—. Most preferably, $X^2$—$X^3$ taken together are —CONH—. Particularly preferred embodiments of $Y^2$ include tetradecan-1-yl, nonan-1-yl, decan-1-yl and 12-methyl-tridecan-1-yl.

Exemplary preferred isolated antimicrobial laspartomycin derivatives according to structural formula II include:

100

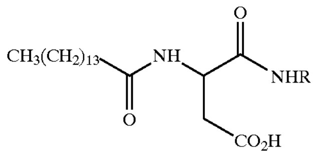

-continued

101

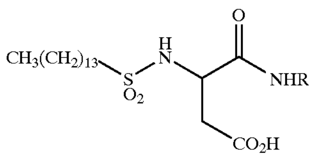

102

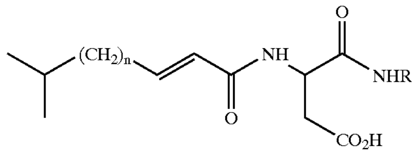

n = 8, 9 or 10

104

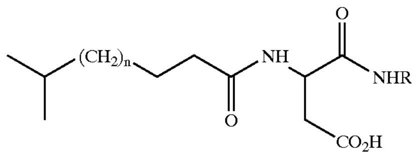

n = 8, 9 or 10

106

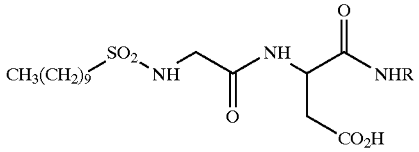

108

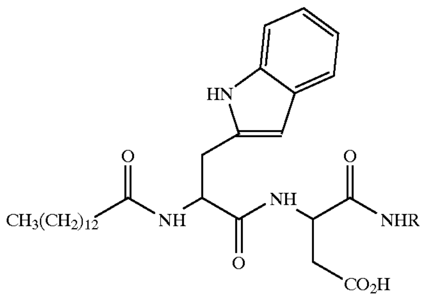

110

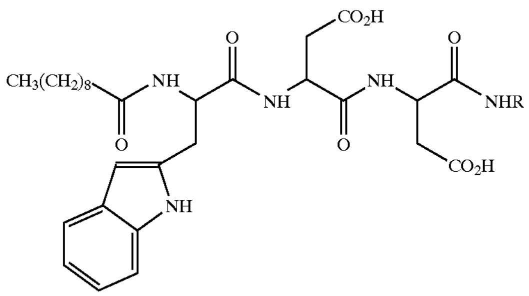

Preferably, in the above depicted embodiments, the polyamide linkers depicted have the L stereochemistry at the α carbon of the illustrated amino acids.

4.2.5 Methods of Making the Antimicrobial Laspartomycin Derivatives

Antimicrobial laspartomycin derivatives may be synthesized from laspartomycin core peptide 6, laspartomycin core peptide 54 and laspartomycin core peptide derivatives of Formula (I). Laspartomycin core peptide derivatives of Formula (I) may be synthesized by the approaches outlined in Section 4.2.2 of this Application. Those of skill in the art will appreciate that other starting materials may be used in the synthesis of antimicrobial laspartomycin derivatives.

A number of general synthetic approaches may be envisioned for converting laspartomycin core peptide 6, laspartomycin core peptide 54 and laspartomycin core peptide derivatives of Formula I to antimicrobial laspartomycin derivatives. These include but are not limited to the approaches outlined in Schemes 4 and 5.

$$Y^2—X^2—X^3—L—X^{1'}+HN(R^1)—R \rightarrow Y^2—X^2—X^3—L—X^1N(R^1)—R$$ Scheme 4

In Scheme 4 a lipophilic fragment $Y^2$ and a linker L, attached via linked groups $X^2$ and $X^3$ are covalently linked to $X^{1'}$ which may be an activated derivative of $X^1$ such as for example, —CO—Z, —OCO—Z, —$SO_2$—Z, —CS—Z, —PO—Z, —OPO—Z, —OC(O)—Z, —NHCO—Z or —$NR^1$CO—Z where Z is a leaving group such as halogen or an activated ester. Methods for making activated derivatives of $X^1$ and for reacting these derivatives with either primary or secondary amines to form the $X^1$—N covalent bond are known to those of skill in the art and may be found in any compendium of standard synthetic methods (See e.g., March, J., *Advanced Organic Chemistry; Reactions, Mechanisms and Structure*, 4th ed., 1992; Larock, R., *Comprehensive Organic Transformations*, VCH: New York, 1999; Bodanzsky, M., *Principles of Peptide Synthesis*; Springer Verlag, 1984; Bodanzsky, M., *Practice of Peptide Synthesis*; Springer Verlag, 1984). Other synthetic methods based on free radical chemistry, photochemistry or electrochemistry for forming the $X^1$—N bond will be apparent to those of skill in the art. Formation of the $X^1$—N covalent bond provides the antimicrobial laspartomycin derivative. Methods for making ($X^2$—$X^3$) linkages such as esters, amides phosphoramidites, sulfonamides, carbamates, ureas etc. are also conventional and known to those of skill in the art (See e.g., March, J., *Advanced Organic Chemistry; Reactions, Mechanisms and Structure*, 4th ed., 1992; Larock, R., *Comprehensive Organic Transformations*; VCH: New York, 1999; Bodanzsky, M., *Principles of Peptide Synthesis*; Springer Verlag, 1984; Bodanzsky, M., *Practice of Peptide Synthesis*; Springer Verlag, 1984)

$$Y^2—X^{2'}+Y^1—L—X^1N(R^1)—R \rightarrow Y^2—X^2—X^3—L—X^1N(R^1)—R$$ Scheme 5

Scheme 5 describes a convergent approach where $Y^2$—$X^{2'}$ ($X^{2'}$ is a derivative of the linked group $X^2$) and $Y^1$—L—$X^1N(R^1)$—R are combined to form the ($X^2$—$X^3$) linkage thus providing the antimicrobial laspartomycin derivative. Methods for forming the ($X^2$—$X^3$) linkage are described above. Fragments such as $Y^2$—$X^{2'}$ are either commercially available or may be made by standard synthetic methods. $Y^1$—L—$X^1N(R^1)$—R may be made as described in Section 4.2.2 of this application.

Those of skill in the art will appreciate that protection of either $Y^2$ and/or L may be necessary to form ($X^2$—$X^3$) linkage. In the event that protection of either $Y^2$ and/or L is necessary to form the ($X^2$—$X^3$) linkage, then deprotection of either $Y^2$ and/or L will be necessary to provide the antimicrobial laspartomycin derivative. Methods for protection and deprotection of common organic functionalities are known to those of skill in the art and may be used as necessary in the synthesis of antimicrobial laspartomycin derivatives (see e.g. Greene, T. W., *Protective Groups in Organic Synthesis*, 3rd edition, 1999).

4.2.6 Methods of Inhibiting Microbial Growth

Generally, active isolated antimicrobial laspartomycin derivatives of the invention are identified using in vitro screening assay. Indeed, in many instances the isolated antimicrobial laspartomycin derivatives of the invention will be used in vitro as preservatives, topical antimicrobial treatments, etc. Additionally, despite certain apparent limitations of in vitro susceptibility tests, clinical data indicate that a good correlation exists between minimal inhibitory concentration (MIC) test results and in vivo efficacy of antibiotic compounds (Murray, 1994, *Antimicrobial Susceptibility Testing*, Poupard et al., eds., Plenum Press, N.Y.; Knudsen et al., 1995, *Antimicrob. Agents Chemother*. 39 (6):1253–1258). Thus, isolated antimicrobial laspartomycin derivatives useful for treating infections and diseases related thereto are also conveniently identified by demonstrated in vitro antimicrobial activity against specified microbial targets.

Generally, the in vitro antimicrobial activity of antimicrobial agents is tested using standard NCCLS bacterial inhibition assays, or MIC tests (see, National Committee on Clinical Laboratory Standards "Performance Standards for Antimicrobial Susceptibility Testing," NCCLS Document M100-S5 Vol. 14, No. 16, December 1994; "Methods for dilution antimicrobial susceptibility test for bacteria that grow aerobically-Third Edition," Approved Standard M7-A3, National Committee for Clinical Standards, Villanova, Pa.).

Alternatively, the antimicrobial laspartomycin derivatives of the invention may be assessed for antimicrobial activity using in vivo models. Again, such models are well-known in the art.

It will be appreciated that other assays, that are well known in the art or which will become apparent to those having skill in the art upon review of this disclosure, may also be used to identify active isolated antimicrobial laspartomycin derivatives of the invention. Such assays include, for example, the assay described in Lehrer et al., 1988, *J. Immunol. Methods* 108:153 and Steinberg and Lehrer, "Designer Assays for Antimicrobial Peptides: Disputing the 'One Size Fits All' Theory," In: *Antibacterial Peptide Protocols*, Shafer, Ed., Humana Press, N.J.

Generally, isolated antimicrobial laspartomycin derivatives of the invention will exhibit MICs of less than about 64 μg/mL, usually less than about 32 μg/mL, preferably less than about 16 μg/mL and most preferably less than about 4 μg/mL. The antimicrobial laspartomycin derivatives of the invention may also exhibit antifungal activity, having MICs of about 50 μg/mL or less against a variety of fungi in standard in vitro assays.

Of course, compounds having MICs on the low end of these ranges, or even lower, are preferred. Most preferred for use in treating or preventing systemic infections are antimicrobial laspartomycin derivatives that exhibit significant antimicrobial activity (i.e., less than 4 μg/mL), good water-solubility (at approx. neutral pH) and low toxicity. Toxicity is less of a concern for topical administration, as is water solubility.

4.2.7 Other Methods and Pharmaceutical Compositions

The antimicrobial laspartomycin derivatives of the invention can be used in a wide variety of applications to inhibit the growth of microorganisms or kill microorganisms. For example, the antimicrobial laspartomycin derivatives may be used as disinfectants or as preservatives for materials such as foodstuffs, cosmetics, medicaments and other nutrient containing materials. The antimicrobial laspartomycin derivatives can also be used to treat or prevent diseases related to microbial infection in subjects such as plants and animals.

For use as a disinfectant or preservative, the antimicrobial laspartomycin derivatives can be added to the desired material singly, as mixtures of antimicrobial laspartomycin derivatives, or in combination with other antifungal and/or antimicrobial agents. The antimicrobial laspartomycin derivatives may be supplied as the compound per se or may be in admixture with a variety of carriers, diluents or excipients, which are well known in the art.

When used to treat or prevent microbial infections or diseases related thereto the antimicrobial laspartomycin derivatives of the invention can be administered or applied singly, as mixtures of two or more antimicrobial laspartomycin derivatives, in combination with other antifungal, antibiotic or antimicrobial agents or in combination with other pharmaceutically active agents. The antimicrobial laspartomycin derivatives can be administered or applied per se or as pharmaceutical compositions. The specific pharmaceutical formulation will depend upon the desired mode of administration, and will be apparent to those having skill in the art. Numerous compositions for the topical or systemic administration of antibiotics are described in the literature. Any of these compositions may be formulated with the antimicrobial laspartomycin derivatives of the invention.

Pharmaceutical compositions comprising the antimicrobial laspartomycin derivatives of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active antimicrobial laspartomycin derivatives into preparations which can be used pharmaceutically. Proper formulation is dependent upon the route of administration chosen.

For topical administration the antimicrobial laspartomycin derivatives of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, the antimicrobial laspartomycin derivatives of the invention may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

Alternatively, the antimicrobial laspartomycin derivatives may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the antimicrobial laspartomycin derivatives can be readily formulated by combining them with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compositions may take the form of tablets, lozenges, etc. formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The antimicrobial laspartomycin derivatives may also be formulated in rectal or vaginal compositions such as suppositories or retention enemas, e.g. containing conventional suppository bases such as cocoa butter or other glycerides.

In addition to the formulations described previously, the antimicrobial laspartomycin derivatives may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver the antimicrobial laspartomycin derivatives of the invention. Certain organic solvents such as dimethylsulfoxide also may be employed, although usually at the cost of greater toxicity. Additionally, the antimicrobial laspartomycin derivatives may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few weeks up to over 100 days.

As certain of the carboxylic acids of the antimicrobial laspartomycin derivatives of the invention are acidic, or the lipophilic group or linker may include acidic or basic substituents, the antimicrobial laspartomycin derivatives may be included in any of the above-described formulations as the free acids, the free bases or as pharmaceutically acceptable salts. Pharmaceutically acceptable salts are those salts which retain substantially the antimicrobial activity of the free acids or bases and which are prepared by reaction with bases or acids, respectively. Pharmaceutical salts tend to be more soluble in aqueous and other protic solvents than are the corresponding free base or acid forms.

The antimicrobial laspartomycin derivatives of the invention, or compositions thereof, will generally be used in an amount effective to achieve the intended purpose. Of course, it is to be understood that the amount used will depend on the particular application.

For example, for use as a disinfectant or preservative, an antimicrobially effective amount of a antimicrobial laspartomycin derivative, or composition thereof, is applied or added to the material to be disinfected or preserved. By antimicrobial effective amount is meant an amount of antimicrobial laspartomycin derivative or composition that inhibits the growth of, or is lethal to, a target microbe. While the actual amount will depend on a particular target microbe and application, for use as a disinfectant or preservative the antimicrobial laspartomycin derivatives, or compositions thereof, are usually added or applied to the material to be disinfected or preserved in relatively low amounts. Typically, the antimicrobial laspartomycin derivatives comprises less than about 5% by weight of the disinfectant solution or material to be preserved, preferably less than about 1% by weight and more preferably less than about 0.1% by weight. An ordinarily skilled artisan will be able to determine antimicrobially effective amounts of particular antimicrobial laspartomycin derivatives for particular applications without undue experimentation using, for example, the in vitro assays provided in the examples.

For use to treat or prevent microbial infections, the antimicrobial laspartomycin derivatives of the invention, or compositions thereof, are administered or applied in a therapeutically effective amount. By therapeutically effective amount is meant an amount effective to ameliorate the symptoms of, or ameliorate, treat or prevent microbial infections. Determination of a therapeutically effective amount is well within the capabilities of those skilled in the art, especially in light of the detailed disclosure provided herein.

As in the case of disinfectants and preservatives a therapeutically effective dose, for topical administration to treat or prevent microbial, yeast, fungal or other infection, can be determined using, for example, the in vitro assays provided in the examples. The treatment may be applied while the infection is visible, or even when it is not visible. An ordinarily skilled artisan will be able to determine therapeutically effective amounts to treat topical infections without undue experimentation.

For systemic administration, a therapeutically effective dose can be estimated initially from in vitro assays. For example, a dose can be formulated in animal models to achieve a circulating antimicrobial laspartomycin derivative concentration range that includes the $IC_{50}$ as determined in cell culture (i.e., the concentration of test compound that is lethal to 50% of a cell culture), the MIC as determined in cell culture (i.e., the minimal inhibitory concentration for growth) or the $IC_{100}$ as determined in cell culture (i.e., the concentration of antimicrobial laspartomycin derivative that is lethal to 100% of a cell culture). Such information can be used to more accurately determine useful doses in humans.

Initial dosages can also be estimated from in vivo data, e.g., animal models, using techniques that are well known in the art. One having ordinary skill in the art can readily optimize administration to humans based on animal data.

Alternatively, initial dosages can be determined from the dosages administered of known antimicrobial agents (e.g., laspartomycin) by comparing the $IC_{50}$, MIC and/or $I_{100}$ of the specific antimicrobial laspartomycin derivatives with that of a known antimicrobial agent, and adjusting the initial dosages accordingly. The optimal dosage may be obtained from these initial values by routine optimization.

Dosage amount and interval may be adjusted individually to provide plasma levels of the active antimicrobial laspartomycin derivatives which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering a single daily dose or multiple doses each day.

In cases of local administration or selective uptake, the effective local concentration of antimicrobial laspartomycin derivative may not be related to plasma concentration. One having skill in the art will be able to optimize therapeutically effective local dosages without undue experimentation.

The amount of antimicrobial laspartomycin derivative administered will, of course, be dependent on, among other factors, the subject being treated, the subject's weight, the severity of the affliction, the manner of administration and the judgment of the prescribing physician.

The antimicrobial therapy may be repeated intermittently while infections are detectable, or even when they are not detectable. The therapy may be provided alone or in combination with other drugs, such as for example other antibiotics or antimicrobials, or other antimicrobial laspartomycin derivatives of the invention.

Preferably, a therapeutically effective dose of the antimicrobial laspartomycin derivatives described herein will provide therapeutic benefit without causing substantial toxicity. Toxicity of the antimicrobial laspartomycin derivatives can be determined using standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Antimicrobial laspartomycin derivatives which exhibit high therapeutic indices are preferred. The data obtained from these cell culture assays and animal studies can be used in formulating a dosage range that is not toxic for use in subjects. The dosage of the antimicrobial laspartomycin derivatives described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition (See, e.g. Fingl et al., 1975, In: *The Pharmacological Basis of Therapeutics*, Ch.1, p.1).

5. EXAMPLES

The invention having been described, the following examples are presented to illustrate, rather than to limit, the scope of the invention. The examples illustrate various embodiments and features of the present invention.

5.1 Example 1

Selection of Parent Culture

The parent culture used for biochemical synthesis of laspartomycin is *Streptomyces viridochromogenes* ssp. *komabensis*, (ATCC-29814, BSP-M728) which was selected as follows. A cell suspension of *Streptomyces viridochromogenes* ssp. *komabensis*, (ATCC-29814) was diluted so that plating on a nutrient medium gave well separated single colonies after incubation at about 28° C. A few colonies were isolated and tested by fermentation for improvement in laspartomycin yield on the basis of morphological observations (colony size, surface structure, edge profile, etc.) which are within the capabilities of those of skill in the art. The colony BSP-M728/1, provided higher and more reproducible yields and yielded superior correlation with mycelial density in the fermentation mash. Thus, for at least these reasons, *Streptomyces viridochromogenes* ssp. *komabensis*, (ATCC-29814, BSP-M728) was selected for biochemical synthesis of laspartomycin.

5.2 Example 2

Medium Inoculation

Ideally, the biochemical synthesis of laspartomycin is performed by inoculating a medium composed of about 3.0% trypticase soy broth, about 1.0% corn dextrin and 0.1% $CaCO_3$ in tap water with spore and mycelial scrapings from a slant of *Streptomyces viridochromogenes* ssp. *komabensis*, (ATCC-29814, BSP-M728). Incubation of about 50 mL of the inoculated medium at 28° C. on a rotary shaker at about revolutions per minute ("RPM") for about 48 hours provides a substantial and uniform vegetative growth. The growth may then be used to inoculate various fermentation media (See, e.g., Example 3). Preferably, the growth comprises a concentration range of between about 2.0% to about 3.0% of the fermentation medium when used to inoculate fermentation medium.

5.3 Example 3

Shaker Flask Fermentation

The inoculum produced in Example 2 may be used to seed a number of fermentation media such as: (1) a medium containing about 2.0% dextrose, about 0.5% beef extract, about 0.5% peptone, about 0.5% NaCl and about 0.35% $CaCO_3$ in water; (2) a medium containing about 0.5% dextrose, about 1.5% dextrin, about 1.0% molasses, about 1.0% peptone and about 0.1% $CaCO_3$ dissolved in water; and (3) a medium containing about 0.5% dextrose, about 1.5% glycerol, about 0.75% peptone, about 0.2% NaCl and about 0.1% $CaCO_3$ in water. In typical shaker flask fermentations, about 50 mL of the above media are seeded with the inoculum of Example 2 and are incubated at a temperature of about 28° C. on a rotary shaker at between about 160 and about 180 RPM for a period of between about 4 and about 7 days.

5.4 Example 4

Biochemical Synthesis of Laspartomycin

Biochemical synthesis of laspartomycin is preferably performed in a culture medium containing about 0.5% dextrose, about 1.5% corn dextrin, about 0.75% Soytone, 0.3% NaCl, about 0.1% $MgSO_4.7H_2O$ and about 0.1% $CaCO_3$ in water. The unadjusted pH of this medium is generally between about 7.2 and about 7.3. The inoculated medium is incubated at a temperature of between about 24° C. to about 34° C. (preferably between about 27° C. to about 29° C., most preferably about 28° C.) on a rotary shaker at between about 140 and about 200 RPM (preferably between about 160 and about 180 RPM) for a period of between about 4 and about 7 days (preferably, between about 5 and about 6 days) until significant amounts of laspartomycin are synthesized. Harvest pH readings of the medium are between about 8.0 and about 8.6. The yield for laspartomycin is about 600 mg/liter of fermentation medium, while the yield of the C-15 laspartomycin derivative is about 400 mg/liter of fermentation medium. The medium formulation and the quantitative ratio of its members has a direct effect on the ratio of the individual lipopeptide components of laspartomycin.

5.5 Example 5

Separation of Laspartomycin from Fermentation Broth

About 1.85 liters of fermentation broth produced by the method of Example 4 at pH of about 8.5 was mixed with an equal volume of 1-butanol and the phases allowed to separate. The dark brown aqueous phase was discarded and the slightly colored 1-butanol phase containing laspartomycin was combined with an equal amount of distilled water, stirred and the pH of the mixture was adjusted to about 2.0 with 1 NHCl. The phases were separated and the 1-butanol phase was washed with ¼ its volume of water, mixed with an equal volume of water and the pH of the mixture was adjusted to about 7.0. The phases again were separated and the pH of the aqueous phase containing laspartomycin was adjusted to about 2.0 and laspartomycin was extracted into 1-butanol and then back into the aqueous phase at a pH of about 7.0. The aqueous phase contained laspartomycin as the partial sodium salt. The solution was evaporated under vacuum to remove residual 1-butanol and then lyophilized to provide about 561 mg of the sodium salt of laspartomycin as a white powder.

5.6 Example 6

Separation of Laspartomycin from Fermentation Broth

About 1.8 liters of fermentation broth produced by the method of Example 4 was adjusted to about pH 2.0 and allowed to stand at about 4° C. for three hours. The cells and any precipitate were separated by centrifugation and suspended in about 500 mL of water. The pH of the suspension was adjusted to about 7.0 with 1N NaOH and the resulting mixture was stirred at room temperature for approximately one hour. Calcium chloride (about 500 mg) was added to the suspension and the pH of the mixture was adjusted to between about 8.6 and about 9.0 with 1.0 N NaOH. Laspartomycin was extracted from the aqueous suspension by two sequential washings with about 500 mL and then about 100 mL of 1-butanol. While not wishing to be bound by theory, laspartomycin may form a chelate with the added calcium ion. The combined butanol extracts were mixed with an equal volume of distilled water, adjusted to about pH 2.0 with 1 N HCl and rinsed twice with 200 mL of distilled water maintained at about pH 2.0. While not wishing to be bound by theory, the laspartomycin calcium chelate may be disrupted by acidic solutions and calcium ion may be removed by washing with acidic water. The 1-butanol phase containing the antibiotic was separated, mixed with an equal volume of distilled water and the mixture adjusted to about pH 7.0 with 1N NaOH to provide laspartomycin in the aqueous phase. The aqueous phase was separated and laspartomycin was then extracted into 1-butanol at about pH 3.0 and then into an aqueous phase at about pH 7.0. The clear almost colorless aqueous phase was evaporated under vacuum to remove residual 1-butanol and freeze-dried to obtain 668 mg of the sodium salt of laspartomycin as a white powder.

HPLC of the salt indicated that about 80% of the salt was the C-15 component of laspartomycin. High resolution FAB-mass spectroscopy: calculated for $C_{57}H_{90}N_{12}O_{19}$+Na $(M+Na)^+$, 1269.6343, found, 1269.6289 which corresponds to a molecular formula $C_{57}H_{90}N_{12}O_{19}$ for the C-15 component of laspartomycin.

Laspartomycin was hydrolyzed with 6N HCl at 120° C. for 16 hours. Amino acid analysis provided the following amino acids in the indicated molar ratios: aspartic acid (3 moles), glycine (3 moles), pipecolic acid (1 mole), allo-threonine (1 mole), isoleucine (1 mole), diaminopropionic acid (1 mole) and proline (1 mole).

5.7 Example 7

Preparation of the Acid Form of Laspartomycin

The acid form of laspartomycin was prepared by dissolving about 100 mg of the sodium salt prepared as described in Example 6 into about 10 mL of water and adjusting the pH of the solution to about 2.0 with 0.1 N HCl. The aqueous solution was extracted with about 10 mL of 1-butanol. The organic extract was then washed with about 5 mL of water, mixed with about another 20 mL of water, evaporated under vacuum to obtain an aqueous solution of laspartomycin as the carboxylic acid and freeze-dried to obtain about 77 mg of white powder. FAB-MS m/z:1248 $(M+H)^+$, 1270$(M+Na)^+$, and 1286 $(M+K)^+$ which corresponds to a molecular formula of $C_{57}H_{90}N_{12}O_{19}$ for the C-15 component of laspartomycin. Elemental analysis: found: C, 52.13; H, 7.58; H, 11.83; O, 28.34.

5.8 Example 8

Selection of Deacylase Microorganism and Biochemical Synthesis of Deacylase

*Actinoplanes utahensis* NRRL 12052 was cultured under submerged aerobic fermentation conditions to provide the deacylase. Because single-colony isolates of the culture were heterogeneous for both morphology and enzyme production capability, selections were made to recover a stable, high-producing variant. Initially, multiple fermentations were carried out using inocula prepared from strain 12052. Vegetative growth yielding the highest deacylating activity was plated on a differential agar, such as CM agar, which contains 0.5% corn steep liquor, 0.5% Bacto peptone, 1.0% soluble starch, 0.05% NaCl, 0.05% $CaCl_2$-$2H_2O$ and 2.0% Bacto agar. Colonies were then selected for further evaluation. Generally, small colonies were better enzyme producers than the large colony types. Isolate No. 18 was the highest deacylase producer selected and was routinely used for the production of the deacylase enzyme.

The high-producing, natural variant was used in a known fermentation protocol (Boeck et al., 1988, *J. Antibiot.*, 41, 1085). A mycelial suspension of the high producing NRRL 12052 variant was grown from a stock culture (preserved in 20% glycerol at −70° C.) in about 10 mL of a medium, which contained about 2.0% sucrose, about 2.0% precooked oatmeal, about 0.5% distiller's grain, about 0.25% yeast, about 0.1% $K_2HPO_4$, 0.05% KCl, about 0.05% $MgSO_4$-$7H_2O$ and about 0.0002% $FeSO_4$-$7H_2O$ in deionized water at about 30° C. for about 72 hrs on a rotary shaker orbiting at about 250 RPM. The mycelial suspension was transferred to about 50 mL of PM3 medium, which contained about 2% sucrose, about 1.0% peanut meal, about 0.12% $K_2HPO_4$, about 0.05% $KH_2PO_4$ and about $MgSO_4$-$7H_2O$ in tap water and incubated at a temperature of about 30° C. for a period of about 60 to about 90 hrs.

5.9 Example 9

Synthesis of Compound 6

Two hundred fifty-seven milligrams of laspartomycin in about 12 mL of 0.5M phosphate buffer of about pH 7.2 was added to about 120 mL of deacylase fermentation broth prepared as in Example 8 and incubated for about 16 hours at about 29° C. at about 180 rpm. The broth was centrifuged, the centrifugate decanted and solids were extracted with about 40 mL of distilled water. The pooled centrifugates were then applied to a 2.5×5.0 cm styrene-divinylbenzene resin column (ENVI™-Chrom P) and the product was eluted with a 10% and 11% acetonitrile-pH 7.2 phosphate mixture. Pooled fractions were concentrated and the pH was adjusted to about 4.65 by addition of ammonium acetate-acetic acid buffer. The fractions were then applied to a 2.5×5.0 cm resin column (ENVI™-Chrom P). The desired material was eluted 12.5% acetonitrile-pH 4.65 acetate mixture. The pH of the pooled fractions was adjusted to about 7.8, followed by concentration and freeze-dried to provide about 74 mg of 6 as an off-white solid which was about 97% pure when analyzed by ("High Pressure Liquid Chromatography") HPLC at 215 nm. FAB-MS m/z 910 (HR-FAB-MS of 6: found 910.4251$(M+H)^+$, calc. 910.4270 for $C_{38}H_{59}N_{11}O_{15}$+H). Also obtained was about 14 mg of an isomer of 6 as an off white solid. FAB-MS: m/z 910$(M+H)^+$.

6.10 Example 10

Synthesis of Compound 6 and Compound 54

About 2.5 g of laspartomycin was treated with the deacylase broth under conditions similar to those described in Example 9 except where explicitly noted. About 1.0 g of laspartomycin was treated with deacylase at about 2.0 mg/mL for about 3.7 hrs to produce a sample enriched in 54. About 1.5 g of laspartomycin was treated with deacylase at about 5.0 mg/mL for about 20 hours. The fermentation broths were pooled and then processed as described in Example 9 to provide about 100 mg of 54, about 600 mg of 6, and an estimated 150 mg of the isomer of 6. FAB-MS of 54: m/z 1026$(M+H)^+$,1048$(M+Na)^+$.

5.11 Example 11

Synthesis of Pentadecanoyl-L-aspartic-acid-4-O-benzyl Ester

Equimolar amounts of pentadecanoic acid, dicyclohexylcarbodiimide, and 1-hydroxybenzotriazole in tetrahydroflran was stirred overnight and the reaction mixture was filtered and evaporated to give a crystalline solid. The solid was then slurried in ethyl acetate, filtered and dried to provide pentadecanoyl-1-hydroxybenzotriazole ester. L-aspartic acid 4-O-benzyl ester (0.2578 g, 1.156 mmol) was added to 2 mL of water and 2 mL of tetrahydrofuran followed by 1 mL of saturated sodium bicarbonate solution and stirred until dissolved. A slurry of pentadecanoyl-hydroxybenzotriazole (0.2798 g, 0.758 mmol) in 5 mL of water and 5 mL of tetrahydrofuran was added and the reaction mixture was stirred at ambient temperature overnight. The reaction mixture was then poured into 20 mL of water and acidified to about pH 1.0 with 6N hydrochloric acid. The resulting precipitate was chilled, filtered and dried to afford 0.2792 g. of pentadecanoyl-L-aspartic-acid-4-O-Benzyl ester in 79% yield. FAB-MS: m/z 448 $(M+H)^+$, 470 $(M+Na)^+$, 492 $(M+2Na-H)^+$.

5.12 Example 12

Synthesis of Pentdecanoyl-L-aspartic-acid-4-O-benzyl-hydroxybenzotriazole Ester A mixture of pentadecanoyl-L-aspartic-acid-4-O-benzyl ester (0.2619 g, 0.5851 mmol), 1-hydroxybenzotriazole (0.0895 g, 0.5851 mmol), and dicyclohexylcarbodiimde (0.1205 g, 0.5851 mmol) in 5.0 mL of tetrahydrofuran was stirred at room temperature overnight. The reaction mixture was filtered and evaporated to dryness at reduced pressure. The resulting oil was slurred in hexane to give 0.2933 g of pentadecanoyl-L-aspartic-acid-4-O-benzyl-hydroxybenzotriazole ester as a crystalline product (88% yield).

5.13 Example 13

Synthesis of the Benzyl Ester of 100

A mixture of 6 (14.8 mg, 0.0162 mmol) and diisopropylethylamine (0.023 mL, 0.1319 mmol) was added to 0.5 mL of dimethylformamide and stirred at room temperature. Aliquots (0.20 mL) of a solution of the hydroxybenzotriazole ester (44.9 mg, 0.0794 mmol) prepared in Example 12 were added to the solution of laspartomycin core peptide derivative over 5 hours. Water was then added and the reaction mixture adsorbed on a 2.5×5.0 cm styrene-divinylbenzene resin column (ENVI™-Chrom P), and eluted with pH 7.2 phosphate buffer containing about 45% acetonitrile. Fractions containing the desired product were desalted and freeze dried to obtain 6.0 mg of white powder, the benzyl ester of 100. FAB-MS: m/z 1339 $(M+H)^+$, 1361 $(M+Na)^+$, and 1377 $(M+K)^+$.

5.14 Example 14

Synthesis of 100

A mixture of 3.0 mg of the benzyl derivative prepared in Example 13, 11 mg of 5% palladium on carbon and 1.0 mL of methanol was hydrogenated at atmospheric pressure overnight. The mixture was filtered through Celite, evaporated to dryness, slurried in water and lyophilized to give 2.0 mg of 100. FAB-MS: m/z 1287 $(M+K)^+$, 1309 $(M+K+Na-H)^+$.

5.15 Example 15

Synthesis of Dihydro-Laspartomycin

A mixture of 21.3 mg of laspartomycin, 35 mg of 5% palladium on carbon and 25 mL of methanol was hydrogenated at atmospheric pressure overnight (balloon technique). The mixture was filter through Celite, evaporated to dryness, slurried in water and lyophilized to give 19.4 mg of dihydro-laspartomycin. FAB-MS: m/z 1250 $(M+H)^+$, 1272 $(M+Na)^+$.

5.16 Example 16

Synthesis of the Protected Derivative of 54 t-Butoxycarbonyl-L-aspartic acid 4-O-benzyl-1-hydroxybenzotriazole ester was prepared from t-butoxycarbonyl-4-O-benzyl-L-aspartic acid, dicyclohexylcarbodiimide, and 1-hydroxybenzotriazole as described in Example 11 and used as described below.

A mixture of 6 (15.2 mg, 0.0167 mmol) and diisopropylethlyamine (0.025 mL, 0.1437 mmol) in 0.20 mL of dimethylformamide was stirred at room temperature under nitrogen. A solution of t-butyoxycarbonyl-L-aspartic acid-4-O-t-butyl-hydroxybenzotriazole ester (0.030 mL aliquots) containing 0.0496 mg (0.1218 mmol) of the activated ester in 0.20 mL was initially added and again after 0.50 hr. The progress of the reaction was followed by HPLC. When the reaction was complete the product was isolated as described in Example 13. Yield of the protected derivative of 54 was 9.0 mg, estimated 90% pure based on HPLC. FAB-MS: m/z 1182 $(M+H)^+$, 1204 $(M+Na)^+$.

5.17 Example 17

Synthesis of 54

0.35 mL of trifluoroacetic acid was added to 6.9 mg of the compound prepared in Example 16 and the solution was allowed to stand at room temperature for 1.5 hr. Trifluoroacetic acid was removed and the residue was lyophilized to afford 4.8 mg of 54 as the trifluoroacetate salt. FAB-MS: m/z 1025 $(M+H)^+$, 1047 $(M+Na)^+$, 1063 $(M+K)^+$.

5.18 Example 18

Synthesis of 100

A solution of 54 (40 mg, 0.039 mmol) in 0.70 mL of dimethylformamide containing 0.050 mL of diisopropylethylamine (0.288 mmol) was stirred at room temperature and 0.35 mL of a solution containing pentadecanoyl-1-hydroxybenzotriazole ester in dimethylformamide, 41 mg (0.112 mmol)was added. After a 1.0 hour period and after a 2.0 hour period an additional 0.17 mL and 0.25 mL of this solution was respectively added. Diisopropylethylamine (0.025 mL) was added after 1.5 hours. The progress of the reaction was followed by HPLC. The product 100 was isolated by the general procedures described in Example 13 except that the solvent to elute the product from the styrene-divinylbenzene resin column (ENVI™-Chrom P) was 33% acetonitrile in water to provide 35 mg of a white powder, estimated 96% pure by HPLC. FAB-MS: m/z 1250$(M+H)^+$, 1272$(M+Na)^+$.

Although the foregoing invention has been described in some detail to facilitate understanding, it will be apparent that certain changes and modifications may be practiced within the scope of the appended claims. Accordingly, the present embodiments are to be considered as illustrative and not restrictive, and the invention is not to be limited to the details given herein, but may be modified within the scope and equivalents of the appended claims.

We claim:

1. A method for making a laspartomycin core peptide, salt or hydrate thereof, comprising the steps of:

culturing *Streptomyces viridochromogenes*, ssp. *komabensis* (ATCC 29814) in a culture medium;

isolating laspartomycin from the culture medium; and cleaving a lipophilic fragment from the laspartomycin, thereby yielding a laspartomycin core peptide, or a salt or hydrate thereof.

2. The method of claim 1 further including the step of isolating the laspartomycin core peptide.

3. The method of claim 1 in which the culturing step is carried out at a temperature in the range of about 24° C. to about 34° C.

4. The method of claim 3 in which the temperature is in the range of about 27° C. to about 29° C.

5. The method of claim 1 in which the microorganism is removed from the culture medium prior to isolating the laspartomycin.

6. The method of claim 5 in which the culture medium is acidified prior to removing the microorganism.

7. The method of claim 6 in which the culture medium is acidified to a pH in the range of about pH 2.0 to about pH 3.0.

8. The method of claim 7 in which the microorganism is removed via centrifugation and suspended in water, thereby providing an aqueous suspension.

9. The method of claim 8 in which the pH of the aqueous suspension is adjusted to a basic pH.

10. The method of claim 8 in which a divalent cation concentration of the aqueous suspension is adjusted to between about 4 mM to about 10 mM and the pH of the aqueous suspension is adjusted to a basic pH.

11. The method of claim 9 or 10 in which the adjusted pH is in the range of about pH 8.0 to about pH 9.0.

12. The method of claim 10 in which the divalent cation is selected from the group consisting of $Ca^{2+}$, $Mg^{2+}$, and $Zn^{+2}$.

13. The method of either of claim 9 or claim 10, in which the laspartomycin is extracted into a first organic solvent, thereby providing an organic solvent extract of laspartomycin.

14. The method of claim 13 further comprising:

acidifying the organic solvent extract of laspartomycin;

extracting the laspartomycin into a first aqueous solution;

extracting the laspartomycin into a second organic solvent;

extracting the laspartomycin into a second aqueous solution; and concentrating the second aqueous solution to provide a salt of laspartomycin.

15. The method of claim 14 in which the first and second organic solvents are 1-butanol.

16. The method of claim 1 in which the lipophilic fragment is cleaved with an enzyme.

17. The method of claim 16 in which the enzyme is a deacylase.

18. The method of claim 1 in which the cleavage step further comprises:

culturing a microorganism capable of producing a deacylase in a culture medium; and contacting laspartomycin with the culture medium.

19. The method of claim 18 in which the microorganism is *Actinoplanes utahensis* (NRRL 12052).

20. The method of claim 19 in which laspartomycin is contacted with the culture medium for about 16 hours at about 29° C.

21. The method of claim 19 in which laspartomycin is contacted with the culture medium for about 4 hours at about 29° C.

22. The method of claim 20 in which the laspartomycin core peptide has the structure:

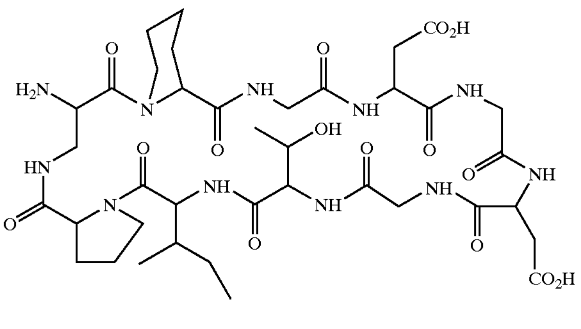

or a salt or hydrate thereof.

23. The method of claim 21 in which the laspartomycin core peptide has the structure:

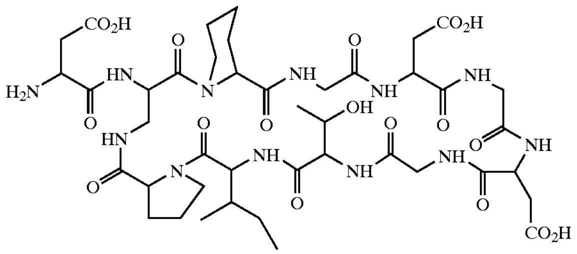

or a salt or hydrate thereof.

24. The laspartomycin core peptide produced by the method of any one of claims 1, 20 and 21.

25. A compound according to structural formula (I):

$$Y^1—L—X^1—N(R^1)—R \quad (I)$$

or a salt or hydrate thereof, wherein:

either (i) $Y^1$—L—$X^1$ taken together is hydrogen; or (ii) $Y^1$ is a linking group;

L is a linker; and $X^1$ is selected from the group consisting of —CO—, —$SO_2$, —CS—, —PO—, —OPO—, —OC(O)—, —NHCO— and —$NR^1$CO—;

N is nitrogen;

$R^1$ is selected from the group consisting of hydrogen, ($C_1$–$C_{10}$) alkyl optionally substituted with one or more of the same or different $R^2$ groups, ($C_1$–$C_{10}$) heteroalkyl optionally substituted with one or more of the same or different $R^2$ groups, ($C_5$–$C_{10}$) aryl optionally substituted with one or more of the same or different $R^2$ groups, ($C_5$–$C_{15}$) arylaryl optionally substituted with one or more of the same or different $R^2$ groups, ($C_5$–$C_{15}$) biaryl optionally substituted with one or more of the same or different $R^2$ groups, five to ten membered heteroaryl optionally substituted with one or more of the same or different $R^2$ groups, ($C_6$–$C_{16}$) arylalkyl optionally substituted with one or more of the same or different $R^2$ groups and six to sixteen membered heteroarylalkyl optionally substituted with one or more of the same or different $R^2$ groups;

each $R^2$ is independently selected from the group consisting of —$OR^3$, —$SR^3$, —$NR^3R^3$, —CN, —$NO_2$, —$N_3$—C(O)$OR^3$, —C(O)$NR^3R^3$, —C(S)$NR^3R^3$, —C($NR^3$)$NR^3R^3$, —CHO, —$R^3$CO, —$SO_2R^3$, —$SOR^3$, —PO($OR^3$)$_2$, —PO($OR^3$)$_2$, —$CO_2$H, —$SO_3$H, —$PO_3$H, halogen and trihalomethyl;

each $R^3$ is independently selected from the group consisting of hydrogen, ($C_1$–$C_6$) alkyl, ($C_5$–$C_{10}$) aryl, 5–10 membered heteroaryl, ($C_6$–$C_{16}$)arylalkyl and six to sixteen membered heteroarylalkyl; and R is a core cyclic peptide of laspartomycin.

26. The compound of claim 25 wherein R has the structure:

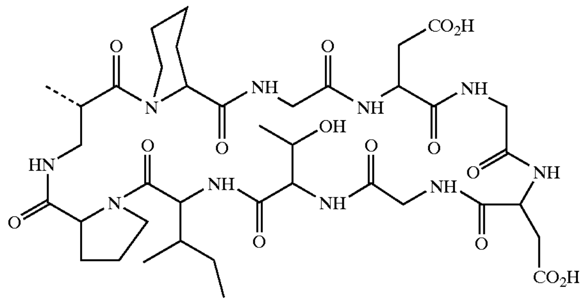

or a salt or hydrate thereof.

27. The compound of claim 26 in which $Y^1$ is selected from the group consisting of —$NHR^1$, —$NH_2$, —OH, —SH, —PH, halogen, —CHO, —$R^1$CO, —$SO_2$H, —$PO_2$H, —$N_3$, —CN, —$CO_2$H, —$SO_3$H, —$PO_3$H, —$PO_2$($OR^1$)H, —$CO_2R^1$, —$SO_3R^1$, and —PO($OR^1$)$_2$.

28. The compound of claim 27 in which $R^1$ is hydrogen.

29. The compound of claim 28 in which $Y^1$ is selected from the group consisting of —SH, $H_2$N—, —OH, —$CO_2$H and —$CO_2R^1$, $X^1$ is carbonyl and L is selected from the group consisting of structures (L1), (L2), (L3), and (L4):

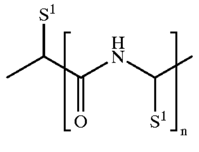

(L1)

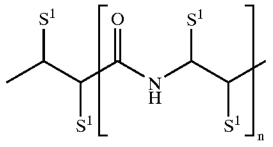

(L2)

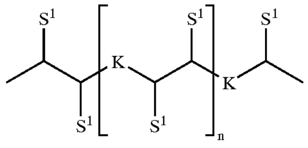

(L3)

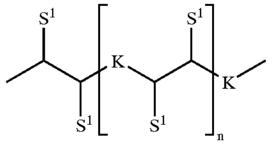

(L4)

or a salt or a hydrate thereof, wherein:

n is 0, 1, 2 or 3;

each $S^1$ is selected from the group consisting of hydrogen, ($C_1$–$C_{10}$) alkyl optionally substituted with one or more of the same or different $R^4$ groups, ($C_1$–$C_{10}$) heteroalkyl optionally substituted with one or more of the same or different $R^4$ groups, ($C_5$–$C_{10}$) aryl optionally substituted with one or more of the same or different $R^4$ groups, ($C_5$–$C_{15}$) arylaryl optionally substituted with one or more of the same or different $R^4$ groups, ($C_5$–$C_{15}$) biaryl optionally substituted with one or more of the same or different $R^4$ groups, five to ten membered heteroaryl optionally substituted with one or more of the same or different $R^4$ groups, ($C_6$–$C_{16}$) arylalkyl optionally substituted with one or more of the same or different $R^4$ groups and six to sixteen membered heteroarylalkyl optionally substituted with one or more of the same or different $R^4$ groups;

each $R^4$ is independently selected from the group consisting of —$OR^5$, —$SR^5$, —$NR^5R^5$, —CN, —$NO_2$, —$N_3$, —$C(O)OR^5$, —$C(O)NR^5R^5$, —$C(S)NR^5R^5$, —$C(NR^5)NR^5R^5$, —CHO, —$R^5CO$, —$SO_2R^5$, —$SOR^5$, —$PO(OR^5)_2$, —$PO(OR^5)$, —$CO_2H$, —$SO_3H$, —$PO_3H$, halogen and trihalomethyl;

each $R^5$ is independently selected from the group consisting of hydrogen, $(C_1–C_6)$ alkyl, $(C_5–C_{10})$ aryl, 5–10 membered heteroaryl, $(C_6–C_{16})$ arylalkyl and six to sixteen membered heteroarylalkyl; and each K is independently selected from the group consisting of oxygen, nitrogen, sulfur and phosphorus.

30. The compound of claim 29 in which each $S^1$ is independently a side-chain of a genetically encoded α-amino acid.

31. The compound of claim 29 in which $Y^1$ is $H_2N$— and L is structure (L1).

32. The compound of claim 31 in which each $S^1$ is independently a side-chain of a genetically encoded α-amino acid.

33. The compound of claim 32 in which n is 0 and $S^1$ is —$CH_2C(O)OH$ or a salt or hydrate thereof.

34. The compound of claim 31 in which L1is —$CH(S^2)$—$[C(O)—NH—CH(S^1)]_n$—, wherein $S^1$ and $S^2$ are each independently a side-chain of a genetically encoded α-amino acid.

35. The compound of claim 34 in which n is 1 and $S^1$ is —$CH_2CO_2H$ or a salt or hydrate thereof and $S^2$ is —$CH_2$-indol-2-yl.

36. The compound of claim 25 in which $Y^1$—L—$X^1$ taken together is hydrogen and $R^1$ is hydrogen.

37. A method for making a laspartomycin core peptide derivative comprising covalently attaching a linker moiety to a laspartomycin core peptide.

38. A method of making an antimicrobial laspartomycin derivative comprising:

covalently attaching a linker moiety to a laspartomycin core peptide, thereby providing a laspartomycin core peptide derivative; and covalently attaching a lipophilic group to the laspartomycin core peptide derivative to yield an antimicrobial laspartomycin derivative.

39. The method of claim 38 farther including the step of isolating the antimicrobial laspartomycin derivative.

40. A method of making an antimicrobial laspartomycin derivative comprising:

covalently attaching a lipophilic group to a linker, thereby providing a lipophilic-linker group; and covalently attaching the lipophilic-linker group to a laspartomycin core peptide, thereby yielding an antimicrobial laspartomycin derivative.

41. The method of claim 40 further including the step of isolating the antimicrobial laspartomycin derivative.

42. The laspartomycin derivative provided by the method of any one of claims 38 and 40.

43. An antimicrobial laspartomycin derivative according to structural formula (II):

$$Y^2—(X^2—X^3)—L—X^1—N(R^1)—R \quad (II)$$

or a pharmaceutically acceptable salt or hydrate thereof, wherein:

$Y^2$ is a lipophilic group;

$X^1$ is selected from the group consisting of —CO—, —$SO_2$—, —CS—, —PO—, —OPO—, —OC(O)—, —NHCO— and —$NR^1CO$—;

$X^2$ is a linked group;

$X^3$ is a linked group;

L is a linker;

N is nitrogen;

$R^1$ is selected from the group consisting of hydrogen, $(C_1–C_{10})$ alkyl optionally substituted with one or more of the same or different $R^2$ groups, $(C_1–C_{10})$ heteroalkyl optionally substituted with one or more of the same or different $R^2$ groups, $(C_5–C_{10})$ aryl optionally substituted with one or more of the same or different $R^2$ groups, $(C_5–C_{15})$ arylaryl optionally substituted with one or more of the same or different $R^2$ groups, $(C_5–C_{15})$ biaryl optionally substituted with one or more of the same or different $R^2$ groups, five to ten membered heteroaryl optionally substituted with one or more of the same or different $R^2$ groups, $(C_6–C_{16})$ arylalkyl optionally substituted with one or more of the same or different $R^2$ groups and six to sixteen membered heteroarylalkyl optionally substituted with one or more of the same or different $R^2$ groups;

each $R^2$ is independently selected from the group consisting of —$OR^3$, —$SR^3$, —$NR^3R^3$, —CN, —$NO_2$, —$N_3$, $C(O)OR^3$, —$C(O)NR^3R^3$, —$C(S)NR^3R^3$, —$C(NR^3)NR^3R^3$, —CHO, —$R^3CO$, —$SO_2R^3$, —$SOR^3$, —$PO(OR^3)_2$, —$PO(OR^3)$, —$CO_2H$, —$SO_3H$, —$PO_3H$, halogen and trihalomethyl;

each $R^3$ is independently selected from the group consisting of hydrogen, $(C_1–C_6)$ alkyl, $(C_5–C_{10})$ aryl, 5–10 membered heteroaryl, $(C_6–C_{16})$ arylakyl and six to sixteen membered heteroarylalkyl; and R is a core cyclic peptide of laspartomycin.

44. The laspartomycin derivative of claim 43 in which R has the structure:

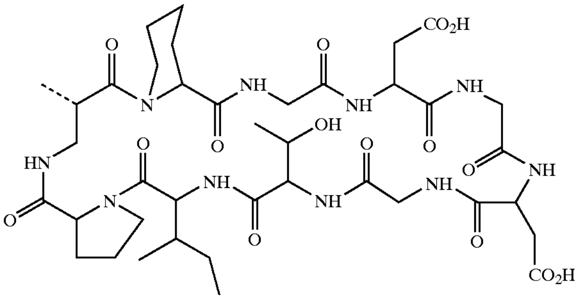

or a salt or a hydrate thereof.

45. The laspartomycin derivative of claim 44 in which $(X^2—X^3)$ taken together are selected from the group consisting of —C(O)O—, —O(O)C—, —CONH—, —NHCO—, —$CONR^1$—, —$NR^1CO$—, —C(O)S—, —S(O)C—, —$OS_2$—, —$S(O_2)O$—, —$NHSO_2$—, $NR^1SO_2$, —$S(O_2)NH$—, —$S(O_2)NR^1$—, C(S)NH—, —NHC(S)—, —NHP(O)—, —P(O)NH—, —OP(O)—, —P(O)O—, —SP(O)—, —P(O)S—, —OC(O)NH—, —NHC(O)O—, —$OC(O)NR^1$—, —$NR^1C(O)O$—, —OC(O)O—, —NHC(O)NH—, —$NHC(O)NR^1$—, —$NR^1C(O)NH$— and $NR^1C(O)NR^1$.

46. The laspartomycin derivative of claim 45 in which $R^1$ is hydrogen.

47. The laspartomycin derivative of claim 46 in which $X^1$ is —CO— or —$SO_2$—, and L is selected from the group consisting of structures (L1), (L2), (L3) and (L4):

(L1)

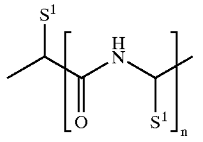

(L2)

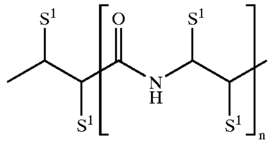

(L3)

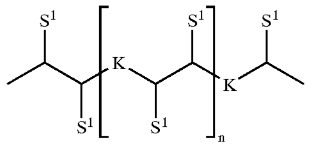

(L4)

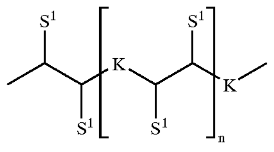

or a pharmaceutically acceptable salt or hydrate thereof, wherein:

n is 0, 1, 2 or 3;

each $S^1$ is selected from the group consisting of hydrogen, ($C_1$–$C_{10}$) alkyl optionally substituted with one or more of the same or different $R^4$ groups, ($C_1$–$C_{10}$) heteroalkyl optionally substituted with one or more of the same or different $R^4$ groups, ($C_5$–$C_{10}$) aryl optionally substituted with one or more of the same or different $R^4$ groups, ($C_5$–$C_{15}$) arylaryl optionally substituted with one or more of the same or different $R^4$ groups, ($C_5$–$C_{15}$) biaryl optionally substituted with one or more of the same or different $R^4$ groups, five to ten membered heteroaryl optionally substituted with one or more of the same or different $R^4$ groups, ($C_6$–$C_{16}$) arylalkyl optionally substituted with one or more of the same or different $R^4$ groups and six to sixteen membered heteroarylalkyl optionally substituted with one or more of the same or different $R^4$ groups;

each $R^4$ is independently selected from the group consisting of —$OR^5$, —$SR^5$, —$NR^5R^5$, —CN, —$NO_2$, —$N_3$, —C(O)$OR^5$, —C(O)$NR^5R^5$, —C(S)$NR^5R^5$, —C($NR^5$)$^{NR5}R^5$, —CHO, —$R^5$CO, —$SO_2R^5$, —$SOR^5$, —PO$(OR^5)_2$, —PO($OR^5$), —$CO_2$H, —$SO_3$H, —$PO_3$H, halogen and trihalomethyl;

each $R^5$ is independently selected from the group consisting of hydrogen, ($C_1$–$C_6$) alkyl, ($C_5$–$C_{10}$) aryl, 5–10 membered heteroaryl, ($C_6$–$C_{16}$)arylalkyl and six to sixteen membered heteroarylalkyl; and each K is independently selected from the group consisting of oxygen, nitrogen, sulfur and phosphorus.

48. The laspartomycin derivative of claim 47 in which each $S^1$ is independently a side-chain of a genetically encoded α-amino acid.

49. The laspartomycin derivative of claim 47 in which L is structure (L1).

50. The laspartomycin derivative of claim 49 in which each $S^1$ is independently a side-chain of a genetically encoded α-amino acid.

51. The laspartomycin derivative of claim 49 in which n is 0.

52. The laspartomycin derivative of claim 51 in which $S^1$ is —$CH_2$—$CO_2$H or a pharmaceutically acceptable salt or hydrate thereof.

53. The laspartomycin derivative of claim 52 in which ($X^2$—$X^3$) taken together are —CONH—.

54. The laspartomycin derivative of claim 53 in which $Y^2$ is tetradecan-1-yl.

55. The laspartomycin derivative of claim 49 in which L is:

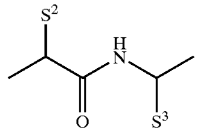

or a salt or hydrate thereof, wherein $S^2$ and $S^3$ are each independently a side chain of a genetically encoded α-amino acid.

56. The laspartomycin derivative of claim 55 in which $S^2$ is —$CH_2$-indol-2-yl and $S^3$ is —$CH_2$—$CO_2$H or a pharmaceutically acceptable salt or hydrate thereof.

57. The laspartomycin derivative of claim 56 in which ($X^2$—$X^3$) taken together are —CONH—.

58. The laspartomycin derivative of claim 57 in which $Y^2$ is nonan-1-yl.

59. The laspartomycin derivative of claim 55 in which $S^2$ is hydrogen and $S^3$ is —$CH_2$—$CO_2$H or a salt thereof.

60. The laspartomycin derivative of claim 59 in which ($X^2$—$X^3$) taken together are —$SO_2$NH—.

61. The laspartomycin derivative of claim 60 in which $Y^2$ is decan-1-yl.

62. The laspartomycin derivative of claim 49 in which L is:

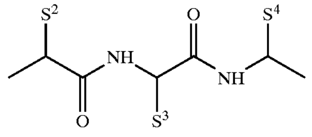

or a salt or hydrate thereof, wherein $S^2$, $S^3$ and $S^4$ are each independently a side chain of a genetically encoded α-amino acid.

63. The laspartomycin derivative of claim 62 in which $S^2$ is —$CH_2$-indol-2-yl, $S^3$ is —$CH_2$—$CO_2$H or a salt thereof and $S^4$ is —$CH_2$—$CO_2$H or a salt thereof.

64. The laspartomycin derivative of claim 63 in which ($X^2$—$X^3$) taken together are —CONH—.

65. The laspartomycin derivative of claim 64 in which $Y^2$ is nonan-1-yl.

66. A pharmaceutical composition comprising a laspartomycin derivative according to claim 42 and a pharmaceutically acceptable excipient, carrier or diluent.

67. A method for treating a microbial infection, said method comprising the step of administering to a subject an effective amount of a laspartomycin derivative according to claim 42.

68. A method of inhibiting microbial growth, said method comprising the step of administering to a microbe an effective amount of a laspartomycin derivative according to claim 42.

69. A pharmaceutical composition comprising a laspartomycin derivative according to any one of claims 43–65 and a pharmaceutically acceptable excipient, carrier or diluent.

70. A method for treating a microbial infection, said method comprising the step of administering to a subject an effective amount of a laspartomycin derivative according to any one of claims 43–65.

71. A method of inhibiting microbial growth, said method comprising the step of administering to a microbe an effective amount of a laspartomycin derivative according to any one of claims 43–65.

72. The method of claim 38 in which the laspartomycin core peptide is provided by a method comprising the steps of:

culturing *Streptomyces viridochromogenes*, ssp. *komabensis* (ATCC 29814) in a culture medium;

isolating laspartomycin from the culture medium; and cleaving a lipophilic fragment from the laspartomycin, thereby yielding the laspartomycin core peptide.

73. The method of claim 72 in which the lipophilic fragment is cleaved with a deacylase.

74. The method of claim 73 in which the deacylase is produced by *Actinoplanes utahensis* (NRRL 12052).

75. The method of claim 38 in which the laspartomycin core peptide has the structure:

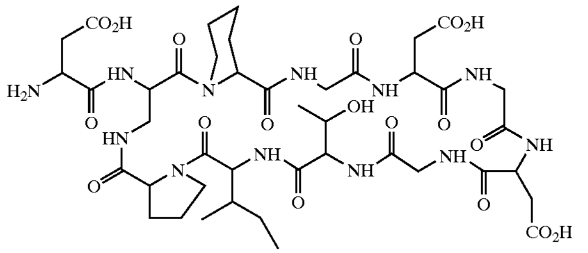

or a salt or hydrate thereof.

76. The method of claim 38 in which the laspartomycin core peptide has the structure:

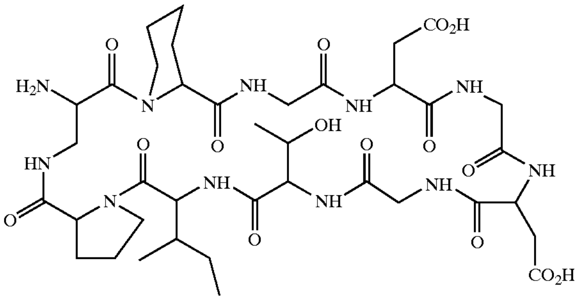

or a salt or a hydrate thereof.

77. The method of claim 40 in which the lipophilic fragment is cleaved with a deacylase.

78. The method of claim 77 in which the deacylase is produced by *Actinoplanes utahensis* (NRRL 12052).

79. The method of claim 40 in which the laspartomycin core peptide has the structure:

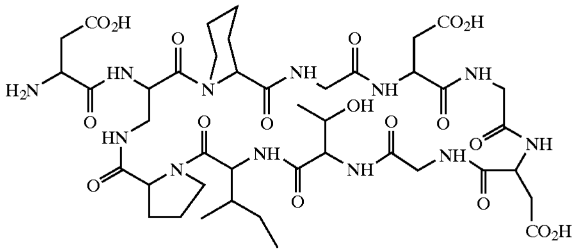

or a salt or a hydrate thereof.

80. The method of claim 40 in which the laspartomycin core peptide has the structure:

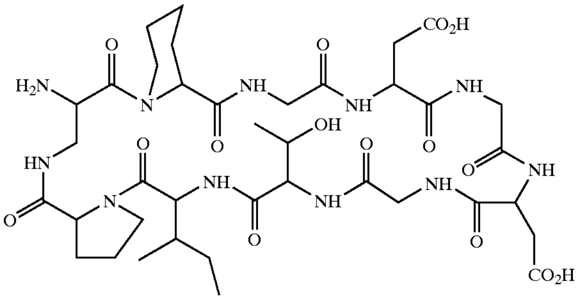

or a salt or a hydrate thereof.

* * * * *

UNITED STATES PATENT AND TRADEMARK OFFICE

CERTIFICATE OF CORRECTION

PATENT NO. : 6,511,962 B1
DATED : January 28, 2003
INVENTOR(S) : Donald B. Borders et al.

It is certified that error appears in the above-identified patent and that said Letters Patent is hereby corrected as shown below:

Column 43,
Line 27, “in which L1is” should read -- in which L1 is --

Column 45,
Line 52, “$-C(NR^{5)NR5}R^5$,” should read -- $-C(NR^5)NR^5R^5$ --

Signed and Sealed this

Twenty-fourth Day of June, 2003

JAMES E. ROGAN
*Director of the United States Patent and Trademark Office*